US007569682B2

(12) United States Patent
Adler et al.

(10) Patent No.: US 7,569,682 B2
(45) Date of Patent: Aug. 4, 2009

(54) BRACHYSPIRA HYODYSENTERIAE VACCINE

(75) Inventors: Ben Adler, Mt. Waverley (AU); Paul Antony Cullen, Murrumbeena (AU); Scott Adam James Coutts, Croydon (AU); Dieter Mark Bulach, Notting Hill (AU); Ruud Philip Antoon Maria Segers, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 31 days.

(21) Appl. No.: 11/833,632

(22) Filed: Aug. 3, 2007

(65) Prior Publication Data

US 2008/0063655 A1    Mar. 13, 2008

Related U.S. Application Data

(63) Continuation of application No. 10/514,054, filed as application No. PCT/EP03/04903 on May 6, 2003, now abandoned.

(30) Foreign Application Priority Data

May 8, 2002    (EP)    ................... 02076800

(51) Int. Cl.
*C07H 21/00* (2006.01)
(52) U.S. Cl. .................................... 536/23.7
(58) Field of Classification Search .................. None
See application file for complete search history.

(56) References Cited

U.S. PATENT DOCUMENTS

| 2004/0186280 A1 | 9/2004 | Hampson et al. |
| 2005/0163791 A1 | 7/2005 | Adler et al. |
| 2006/0057151 A1 | 3/2006 | Hampson et al. |

OTHER PUBLICATIONS

National Center for Biotechnology Information (NCBI;www.ncbi.nlm.nih.gov) Accession No. AAR98524, May 9, 2005.
European Molecular Biology Laboratory—European Bioinformatics Institute (EMBL-EBI;www.ebi.ac.uk/embl) Accession No. AY512344, Jan. 25, 2004.
Cullen, P.A. et al, "Characterization of a locus encoding four paralogous outer membrane lipoproteins of *Brachyspira hyodysenteriae*," Microbes and Infection, vol. 5, p. 275-283 (2003).
Lee, B.J. et al., "Identification of the gene encoding BmpB, a 30 kDa outer envelope lipoprotein . . . ," Veterinary Microbiology, vol. 76, p. 245-257 (2000).
Haake, D.A., "Spirochaetal lipoproteins and pathogenesis," Microbiology, vol. 146, p. 1491-1504 (2000).
Chatfield, S.N. et al., "Identification of the Major Antigens of *Treponema hyodysenteriae* and Comparison with Those of *Treponema innocens*," Infection and Immunity, vol. 56, No. 5, p. 1070-1075 (May 1998).
Lee, B.J. et al., "Production and characterization of a monoclonal antibody to *Serpulina hyodysenteriae*," FEMS Microbiology Letters, vol. 136, p. 193-197 (1996).
Thomas, W. et al., "A 16-Kilodalton Lipoprotein of the Outer Membrane of *Serpulina* (*Treponema*) *hyodysenteriae*," Infection and Immunity, vol. 60, No. 8, p. 3111-3116, (Aug. 1992).

*Primary Examiner*—Robert B Mondesi
*Assistant Examiner*—Brian J Gangle
(74) *Attorney, Agent, or Firm*—Aaron L. Schwartz; William M. Blackstone

(57) ABSTRACT

The present invention relates to nucleic acid sequences encoding a 30 kD *Brachyspira hyodysenteriae* lipoprotein and to parts of such nucleic acid sequences that encode an immunogenic fragment of such lipoproteins, and to DNA fragments, recombinant DNA molecules, live recombinant carriers and host cells comprising such nucleic acid sequences or such parts thereof. The invention also relates to a 30 kD *Brachyspira hyodysenteriae* lipoprotein and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic acid sequences or such parts thereof, lipoproteins or immunogenic parts thereof and antibodies against such lipoproteins or immunogenic parts thereof. Also, the invention relates to the use of said lipoproteins in vaccines and for the manufacture of vaccines. Moreover, the invention relates to the use of said nucleic acid sequences, lipoproteins or antibodies for diagnostic or vaccination purposes. Finally the invention relates to diagnostic kits comprising such a nucleic acid, lipoprotein or antibodies against such lipoprotein.

5 Claims, 8 Drawing Sheets

BlpA        MKKFLLLVSSAILSLMILSCG [SEQ ID NO:23]
BlpE        MKKLLFILFLLSFIISCN [SEQ ID NO: 24]
BlpF        MKSLLIFFLLINILSCN [SEQ ID NO: 25]
BlpG        MKKIILFFTCIFSISCS [SEQ ID NO: 26]
SmpA        MNKKIFTLFLVVAASAIFAVSCN [SEQ ID NO: 22]

FIG. 4.

SEQUENCE LISTING

```
<160> NUMBER OF SEQ ID NOS: 22

<210> SEQ ID NO 1
<211> LENGTH: 4397
<212> TYPE: DNA
<213> ORGANISM: brachyspira hyodysenteriae
<220> FEATURE:
<221> NAME/KEY: CDS
<222> LOCATION: (202)..(996)
<220> FEATURE:
<221> NAME/KEY: CDS
<222> LOCATION: (1031)..(1816)
<220> FEATURE:
<221> NAME/KEY: CDS
<222> LOCATION: (1840)..(2625)
<220> FEATURE:
<221> NAME/KEY: CDS
<222> LOCATION: (2707)..(3522)

<400> SEQUENCE: 1
gtttcagtat atttaaatgg agaatacgga caaaatgatg tttatgcttc tgttcctgct       60
gtacttggaa gaaacggggt tgaagagata atagaaataa aaatgaatga tgatgagaaa      120
aaattatttg atgaatcatg cagtgttatg aaaaagaatt atgaattatc tttgaatatg      180
tgatataaaa ataataatgc t atg aaa aaa ata att tta ttt ttt act tgt        231
                        Met Lys Lys Ile Ile Leu Phe Phe Thr Cys
                        1               5                   10 ata ttt tct att tca tgc tct aat gca aat gaa aat gtt cat att gta        279
Ile Phe Ser Ile Ser Cys Ser Asn Ala Asn Glu Asn Val His Ile Val
            15                  20                  25 aaa gta gga tat ata gga gaa tct gat aaa att att tgg gaa gaa gtt        327
Lys Val Gly Tyr Ile Gly Glu Ser Asp Lys Ile Ile Trp Glu Glu Val
        30                  35                  40 atg aaa aaa gtt tct aat gat aat ata gaa ata gaa ctt gta tct tat        375
Met Lys Lys Val Ser Asn Asp Asn Ile Glu Ile Glu Leu Val Ser Tyr
    45                  50                  55 ata aat tat tct tct cct aat aaa gct ttg aat gat gga gaa att gat        423
Ile Asn Tyr Ser Ser Pro Asn Lys Ala Leu Asn Asp Gly Glu Ile Asp
60                  65                  70 tta aat aat ttt cag cat tat gct ttt ttt aat aat gaa tta gaa aca        471
Leu Asn Asn Phe Gln His Tyr Ala Phe Phe Asn Asn Glu Leu Glu Thr
75                  80                  85                  90 aaa gga tat gag tta act gca ata gcg gat aca tgt ctt gct gct atg        519
Lys Gly Tyr Glu Leu Thr Ala Ile Ala Asp Thr Cys Leu Ala Ala Met
                95                  100                 105
```

```
aat ata tac tct gat aat ata aca aat att aat caa att aaa caa tat      567
Asn Ile Tyr Ser Asp Asn Ile Thr Asn Ile Asn Gln Ile Lys Gln Tyr
        110                 115                 120 gat aga att gcc ata ccc gat gat gat tct aac aga gga aga gct tta      615
Asp Arg Ile Ala Ile Pro Asp Asp Asp Ser Asn Arg Gly Arg Ala Leu
125                 130                 135 aaa gta tta gaa gca gca gga cta ata aaa tta aaa gat aaa tat aaa      663
Lys Val Leu Glu Ala Ala Gly Leu Ile Lys Leu Lys Asp Lys Tyr Lys
        140                 145                 150 ctt aac cct agc ata aat gat ata aaa gaa aat aaa cta aat cta aat      711
Leu Asn Pro Ser Ile Asn Asp Ile Lys Glu Asn Lys Leu Asn Leu Asn
155                 160                 165                 170 atc att gaa gtt gat gct gga agt ata tat act ctg ctt ccg gat att      759
Ile Ile Glu Val Asp Ala Gly Ser Ile Tyr Thr Leu Leu Pro Asp Ile
                175                 180                 185 gca tgc gct gta att aat tgt aat ttt gct tta aac ttc gga ctt gat      807
Ala Cys Ala Val Ile Asn Cys Asn Phe Ala Leu Asn Phe Gly Leu Asp
                190                 195                 200 cct tat aaa gat tca ata ttt aaa gat agt cca agc aac tac aat gat      855
Pro Tyr Lys Asp Ser Ile Phe Lys Asp Ser Pro Ser Asn Tyr Asn Asp
                205                 210                 215 aag aac tat ata aat att ata gct gct aga aca aaa gac aaa gat aat      903
Lys Asn Tyr Ile Asn Ile Ile Ala Ala Arg Thr Lys Asp Lys Asp Asn
        220                 225                 230 gag ata tat aaa aaa ata ata gaa gca tat caa tct gat gag att aaa      951
Glu Ile Tyr Lys Lys Ile Ile Glu Ala Tyr Gln Ser Asp Glu Ile Lys
235                 240                 245                 250 aat ata tat aat aaa aaa ttt aag ggt gtg tat ata gct gtt tgg           996
Asn Ile Tyr Asn Lys Lys Phe Lys Gly Val Tyr Ile Ala Val Trp
                255                 260                 265 taatttaatt ttatagtttt aatgggggga aact atg aaa tct tta tta ata ttt   1051
                                     Met Lys Ser Leu Leu Ile Phe
                                                             270 ttt tta ttg att aat att ctt tct tgt aat gat tct aat att gat att     1099
Phe Leu Leu Ile Asn Ile Leu Ser Cys Asn Asp Ser Asn Ile Asp Ile
                275                 280                 285 att aag gta ggt cat ata gga gaa ttt gat tat gat ata tgg caa aaa     1147
Ile Lys Val Gly His Ile Gly Glu Phe Asp Tyr Asp Ile Trp Gln Lys
        290                 295                 300 ata gac gaa gaa tta caa att gaa aat gcc aaa ttg gat ctg gta tat     1195
Ile Asp Glu Glu Leu Gln Ile Glu Asn Ala Lys Leu Asp Leu Val Tyr
305                 310                 315                 320 ttt gaa gat tat gaa att tta aat aag gca tta gat gac gga gat ata     1243
Phe Glu Asp Tyr Glu Ile Leu Asn Lys Ala Leu Asp Asp Gly Asp Ile
                325                 330                 335 gat ttg aat tct ttt caa aac tat tta tat ttt gta aat gaa act aac     1291
Asp Leu Asn Ser Phe Gln Asn Tyr Leu Tyr Phe Val Asn Glu Thr Asn
                340                 345                 350 aaa tat aat tat aat ctt cat att tta gga aaa act ttt gtg gct cct     1339
Lys Tyr Asn Tyr Asn Leu His Ile Leu Gly Lys Thr Phe Val Ala Pro
        355                 360                 365 atg aat ata tac tca aaa ttt ata act aat ata aat caa ata tca tcg     1387
Met Asn Ile Tyr Ser Lys Phe Ile Thr Asn Ile Asn Gln Ile Ser Ser
370                 375                 380 aat gct aaa ata gct att cct gat gat gaa gtc aat cta tca agg gca     1435
Asn Ala Lys Ile Ala Ile Pro Asp Asp Glu Val Asn Leu Ser Arg Ala
385                 390                 395                 400 ttg caa ata tta gag gtg gca aat ata ata aaa ctt gaa aga ttt gat     1483
Leu Gln Ile Leu Glu Val Ala Asn Ile Ile Lys Leu Glu Arg Phe Asp
                405                 410                 415
```

```
                                                        -continued aac cat ttt tat aat ata tct aat gtc ata gaa aat aat tta aat att     1531
Asn His Phe Tyr Asn Ile Ser Asn Val Ile Glu Asn Asn Leu Asn Ile
        420                 425                 430 cag att ata cct atg gat gct agt ata att tac tac aat atg gat aaa     1579
Gln Ile Ile Pro Met Asp Ala Ser Ile Ile Tyr Tyr Asn Met Asp Lys
            435                 440                 445 gtt gat gcc gca gtt ata aat tac ggt ttc att tca gat tat ata aat     1627
Val Asp Ala Ala Val Ile Asn Tyr Gly Phe Ile Ser Asp Tyr Ile Asn
450                 455                 460 tat aaa att att ttt tat gat gat ata acg caa tat tca cat atg ggt     1675
Tyr Lys Ile Ile Phe Tyr Asp Asp Ile Thr Gln Tyr Ser His Met Gly
465                 470                 475                 480 atg atg tca tat gca aat ctg att gta tgc aga gag aaa gac aaa aat     1723
Met Met Ser Tyr Ala Asn Leu Ile Val Cys Arg Glu Lys Asp Lys Asn
                485                 490                 495 tgt aat ctt tat aaa ttt ata gca gaa agc tac aga caa aaa ata aga     1771
Cys Asn Leu Tyr Lys Phe Ile Ala Glu Ser Tyr Arg Gln Lys Ile Arg
            500                 505                 510 aaa aat ata gaa aaa aat ata tta gac ggt ctc ata gca gtt gac         1816
Lys Asn Ile Glu Lys Asn Ile Leu Asp Gly Leu Ile Ala Val Asp
515                 520                 525 taatattagt ataggaaata tat atg aaa aaa cta tta ttt att tta ttt tta   1869
                        Met Lys Lys Leu Leu Phe Ile Leu Phe Leu
                                530                 535 tta tca ttt att att tca tgt aat tgc aaa aaa gat gaa gta gta aaa     1917
Leu Ser Phe Ile Ile Ser Cys Asn Cys Lys Lys Asp Glu Val Val Lys
        540                 545                 550 ata gga tac ata gga gag ctt gat atg agt ata tgg gaa tat gta tcc     1965
Ile Gly Tyr Ile Gly Glu Leu Asp Met Ser Ile Trp Glu Tyr Val Ser
    555                 560                 565 aat gaa atg aaa gaa aaa aat att att ttg gaa tta ata caa ttt tca     2013
Asn Glu Met Lys Glu Lys Asn Ile Ile Leu Glu Leu Ile Gln Phe Ser
570                 575                 580                 585 gat tat tct ata ata aat aaa gct tta aat agt gga cat ata gat tta     2061
Asp Tyr Ser Ile Ile Asn Lys Ala Leu Asn Ser Gly His Ile Asp Leu
                590                 595                 600 aat cat ttt cag aat tac gct tac ttt gtt aat gcc aca aat aaa aat     2109
Asn His Phe Gln Asn Tyr Ala Tyr Phe Val Asn Ala Thr Asn Lys Asn
            605                 610                 615 gat tat tat ttg agc atc ata gat aaa aca ttt ata gct tct atg aat     2157
Asp Tyr Tyr Leu Ser Ile Ile Asp Lys Thr Phe Ile Ala Ser Met Asn
        620                 625                 630 atg tat tca aaa aat tta acc aat cta tct caa ttg cag ctt aat tct     2205
Met Tyr Ser Lys Asn Leu Thr Asn Leu Ser Gln Leu Gln Leu Asn Ser
    635                 640                 645 aaa ata gca att cca aaa gat gaa gta aat tta tcc aga gct tta aaa     2253
Lys Ile Ala Ile Pro Lys Asp Glu Val Asn Leu Ser Arg Ala Leu Lys
650                 655                 660                 665 ata tta gaa tct ata gga tta tta aaa tta act aaa aag gat aat atc     2301
Ile Leu Glu Ser Ile Gly Leu Leu Lys Leu Thr Lys Lys Asp Asn Ile
                670                 675                 680 aat tat aat ttt act aca aat gat ata aga gaa aat tat tta aaa tta     2349
Asn Tyr Asn Phe Thr Thr Asn Asp Ile Arg Glu Asn Tyr Leu Lys Leu
            685                 690                 695 gag ttt gta gat gta gaa gca gac gat gtt tat tct gta gta tct ttt     2397
Glu Phe Val Asp Val Glu Ala Asp Asp Val Tyr Ser Val Val Ser Phe
        700                 705                 710 gtt gat gct gct ttc gtt aat ctc aat ctt aat ttt gat ttt aaa gat     2445
Val Asp Ala Ala Phe Val Asn Leu Asn Leu Asn Phe Asp Phe Lys Asp
```

-continued

```
          715                 720                 725
tca aat att tta tat tat gat gat cct agc aaa tat gat tct gat atg    2493
Ser Asn Ile Leu Tyr Tyr Asp Asp Pro Ser Lys Tyr Asp Ser Asp Met
730                 735                 740                 745 tat att aat cta ata gct gca aga tta gaa gat gag gat aac agt ctt    2541
Tyr Ile Asn Leu Ile Ala Ala Arg Leu Glu Asp Glu Asp Asn Ser Leu
                750                 755                 760 tat aaa act ata gct gaa gct tat aaa aaa aga ata aaa gag gtt gta    2589
Tyr Lys Thr Ile Ala Glu Ala Tyr Lys Lys Arg Ile Lys Glu Val Val
                765                 770                 775 gaa tca gga aaa tta gag gga att atc atc aat tat taatagtttt         2635
Glu Ser Gly Lys Leu Glu Gly Ile Ile Ile Asn Tyr
                780                 785 tattgaaatt attcaaaaaa taatataatc taaataaatt aatttcatta aaattttata  2695
aaggagcgaa a atg aaa aaa ttt tta tta ttg gta tca tca gcc ata tta   2745
            Met Lys Lys Phe Leu Leu Leu Val Ser Ser Ala Ile Leu
                790                 795                 800 tca tta atg ata tta tca tgc gga aat act tct tct ggt gat caa aag   2793
Ser Leu Met Ile Leu Ser Cys Gly Asn Thr Ser Ser Gly Asp Gln Lys
            805                 810                 815 ata gtt aaa gtt ggt ttt gct gga gag tct gat tat caa att tgg gat   2841
Ile Val Lys Val Gly Phe Ala Gly Glu Ser Asp Tyr Gln Ile Trp Asp
        820                 825                 830 cct ata gta gct aaa tta gct gaa gaa gga att aaa gta gag cta gta   2889
Pro Ile Val Ala Lys Leu Ala Glu Glu Gly Ile Lys Val Glu Leu Val
835                 840                 845                 850 tct ttc tct gat tat act ata cct aat cag gct ttg aat gac gga gaa   2937
Ser Phe Ser Asp Tyr Thr Ile Pro Asn Gln Ala Leu Asn Asp Gly Glu
                855                 860                 865 att gac ttg aat gct ttt cag cat tat gca tac ttt aat gat gaa gta   2985
Ile Asp Leu Asn Ala Phe Gln His Tyr Ala Tyr Phe Asn Asp Glu Val
                870                 875                 880 tca aat aaa gga tat gac tta act gct att gct gat act tat ata tct   3033
Ser Asn Lys Gly Tyr Asp Leu Thr Ala Ile Ala Asp Thr Tyr Ile Ser
            885                 890                 895 gct atg aat att tat tct act aat att act gat gta aaa gaa tta aaa   3081
Ala Met Asn Ile Tyr Ser Thr Asn Ile Thr Asp Val Lys Glu Leu Lys
        900                 905                 910 aac ggc gat aaa ata gct ata cct aat gac cct tct aat gga gga aga   3129
Asn Gly Asp Lys Ile Ala Ile Pro Asn Asp Pro Ser Asn Gly Gly Arg
915                 920                 925                 930 gct tta aaa gtt ctt cag gct gca gga atc att aaa gta aaa cct gaa   3177
Ala Leu Lys Val Leu Gln Ala Ala Gly Ile Ile Lys Val Lys Pro Glu
                935                 940                 945 gca gga gat act cct agc gta aga cta ata ata gaa aat cct cta aat   3225
Ala Gly Asp Thr Pro Ser Val Arg Leu Ile Ile Glu Asn Pro Leu Asn
                950                 955                 960 att gaa ata gta gaa att gga tgc cag gtg cta ttt acc ggt gtt ctt   3273
Ile Glu Ile Val Glu Ile Gly Cys Gln Val Leu Phe Thr Gly Val Leu
                965                 970                 975 cct gat gtt gct tgt gct gtt atc aat gga aac tat gct ata gac ttc   3321
Pro Asp Val Ala Cys Ala Val Ile Asn Gly Asn Tyr Ala Ile Asp Phe
            980                 985                 990 ggt ttg aat cct ggt tct gat tat ata ttc aaa gat gat cct tct       3366
Gly Leu Asn Pro Gly Ser Asp Tyr Ile Phe Lys Asp Asp Pro Ser
995                 1000                1005 att tac agc gga aaa tct ttt gtt aat tta ata gct gca aga act       3411
Ile Tyr Ser Gly Lys Ser Phe Val Asn Leu Ile Ala Ala Arg Thr
1010                1015                1020
```

-continued

```
aaa gat aaa gat aat gaa tta tac aaa aaa gtt gta gaa act tat       3456
Lys Asp Lys Asp Asn Glu Leu Tyr Lys Lys Val Val Glu Thr Tyr
1025                1030                1035 caa tct gaa ata gta gaa aaa gtt tat aat gaa aat ttc tta ggt       3501
Gln Ser Glu Ile Val Glu Lys Val Tyr Asn Glu Asn Phe Leu Gly
1040                1045                1050 tct tat ctt cct act tgg aaa taatataaat attaattgaa taatatttga      3552
Ser Tyr Leu Pro Thr Trp Lys
1055                1060 attataaaaa gaaaagcatg agatttctta ttatctcatg ctttttatt ttgttttta   3612 tatcataata atttaattaa tctaaatcga tatcatcatc ttcttcatct aaagaaggct 3672 ctaatatagc atctttacct gtactcatta tatcattaac taattcatta atatcttctt 3732 tatcagatga aaaatattcc aataacatag caaaattcat tcctgctata agtctaatat 3792 taaatttatt ttctcttttt ttgaaatata tttcctatat taaaaggagt tccgccatat 3852 aaatcagcta atattattat atctttcaca tcattcattt catctaagca gctttgtaat 3912 tttttggaag ttccttcaaa tccgtcatca gctgacatgc atactgtacg atatcctgaa 3972 acttctccta atatcatttt ggcagattcc attatttcat gagcaaaatt accatgactc 4032 ataagtatta aactaggttt catttattcc tccataaata ttttattaat ttcttctctc 4092 aattctaaat aggtattatt atttctattt ggatgaattc tatttgtaag aattatcata 4152 gcctctttag agtttaaatt tattaatata gaagttcctg taaaacctgt atgatataaa 4212 gtatattttc catatctttt atcccagcct aaagttctat ctccaaaatt aatatctatt 4272 aatttttta ttgaactatg agataaaatt ttttcatcat ctttaatata gagcatacaa  4332
aaaatattta aatcttcaag cgtagaaaaa taatcctgca cttcctatct ccctaaaagc 4392 ataag                                                             4397
```

<210> SEQ ID NO 2
<211> LENGTH: 265
<212> TYPE: PRT
<213> ORGANISM: brachyspira hyodysenteriae

<400> SEQUENCE: 2

```
Met Lys Lys Ile Ile Leu Phe Phe Thr Cys Ile Phe Ser Ile Ser Cys
1               5                   10                  15

Ser Asn Ala Asn Glu Asn Val His Ile Val Lys Val Gly Tyr Ile Gly
            20                  25                  30

Glu Ser Asp Lys Ile Ile Trp Glu Glu Val Met Lys Lys Val Ser Asn
        35                  40                  45

Asp Asn Ile Glu Ile Glu Leu Val Ser Tyr Ile Asn Tyr Ser Ser Pro
    50                  55                  60

Asn Lys Ala Leu Asn Asp Gly Glu Ile Asp Leu Asn Phe Gln His
65                  70                  75                  80

Tyr Ala Phe Phe Asn Asn Glu Leu Glu Thr Lys Gly Tyr Glu Leu Thr
                85                  90                  95

Ala Ile Ala Asp Thr Cys Leu Ala Ala Met Asn Ile Tyr Ser Asp Asn
            100                 105                 110

Ile Thr Asn Ile Asn Gln Ile Lys Gln Tyr Asp Arg Ile Ala Ile Pro
        115                 120                 125

Asp Asp Asp Ser Asn Arg Gly Arg Ala Leu Lys Val Leu Glu Ala Ala
    130                 135                 140

Gly Leu Ile Lys Leu Lys Asp Lys Tyr Lys Leu Asn Pro Ser Ile Asn
```

```
                145                 150                 155                 160
Asp Ile Lys Glu Asn Lys Leu Asn Leu Asn Ile Ile Glu Val Asp Ala
                    165                 170                 175
Gly Ser Ile Tyr Thr Leu Leu Pro Asp Ile Ala Cys Ala Val Ile Asn
                180                 185                 190
Cys Asn Phe Ala Leu Asn Phe Gly Leu Asp Pro Tyr Lys Asp Ser Ile
            195                 200                 205
Phe Lys Asp Ser Pro Ser Asn Tyr Asn Asp Lys Asn Tyr Ile Asn Ile
        210                 215                 220
Ile Ala Ala Arg Thr Lys Asp Lys Asp Asn Glu Ile Tyr Lys Lys Ile
225                 230                 235                 240
Ile Glu Ala Tyr Gln Ser Asp Glu Ile Lys Asn Ile Tyr Asn Lys Lys
                245                 250                 255
Phe Lys Gly Val Tyr Ile Ala Val Trp
                260                 265

<210> SEQ ID NO 3
<211> LENGTH: 262
<212> TYPE: PRT
<213> ORGANISM: brachyspira hyodysenteriae

<400> SEQUENCE: 3

Met Lys Ser Leu Leu Ile Phe Phe Leu Leu Ile Asn Ile Leu Ser Cys
1               5                   10                  15
Asn Asp Ser Asn Ile Asp Ile Ile Lys Val Gly His Ile Gly Glu Phe
                20                  25                  30
Asp Tyr Asp Ile Trp Gln Lys Ile Asp Glu Glu Leu Gln Ile Glu Asn
            35                  40                  45
Ala Lys Leu Asp Leu Val Tyr Phe Glu Asp Tyr Glu Ile Leu Asn Lys
        50                  55                  60
Ala Leu Asp Asp Gly Asp Ile Asp Leu Asn Ser Phe Gln Asn Tyr Leu
65                  70                  75                  80
Tyr Phe Val Asn Glu Thr Asn Lys Tyr Asn Tyr Asn Leu His Ile Leu
                85                  90                  95
Gly Lys Thr Phe Val Ala Pro Met Asn Ile Tyr Ser Lys Phe Ile Thr
                100                 105                 110
Asn Ile Asn Gln Ile Ser Ser Asn Ala Lys Ile Ala Ile Pro Asp Asp
            115                 120                 125
Glu Val Asn Leu Ser Arg Ala Leu Gln Ile Leu Glu Val Ala Asn Ile
        130                 135                 140
Ile Lys Leu Glu Arg Phe Asp Asn His Phe Tyr Asn Ile Ser Asn Val
145                 150                 155                 160
Ile Glu Asn Asn Leu Asn Ile Gln Ile Ile Pro Met Asp Ala Ser Ile
                165                 170                 175
Ile Tyr Tyr Asn Met Asp Lys Val Asp Ala Ala Val Ile Asn Tyr Gly
                180                 185                 190
Phe Ile Ser Asp Tyr Ile Asn Tyr Lys Ile Ile Phe Tyr Asp Asp Ile
            195                 200                 205
Thr Gln Tyr Ser His Met Gly Met Met Ser Tyr Ala Asn Leu Ile Val
        210                 215                 220
Cys Arg Glu Lys Asp Lys Asn Cys Asn Leu Tyr Lys Phe Ile Ala Glu
225                 230                 235                 240
Ser Tyr Arg Gln Lys Ile Arg Lys Asn Ile Glu Lys Asn Ile Leu Asp
                245                 250                 255
```

```
Gly Leu Ile Ala Val Asp
            260

<210> SEQ ID NO 4
<211> LENGTH: 262
<212> TYPE: PRT
<213> ORGANISM: brachyspira hyodysenteriae

<400> SEQUENCE: 4

Met Lys Lys Leu Leu Phe Ile Leu Phe Leu Ser Phe Ile Ile Ser
1               5                   10                  15

Cys Asn Cys Lys Lys Asp Glu Val Val Lys Ile Gly Tyr Ile Gly Glu
            20                  25                  30

Leu Asp Met Ser Ile Trp Glu Tyr Val Ser Asn Glu Met Lys Glu Lys
            35                  40                  45

Asn Ile Ile Leu Glu Leu Ile Gln Phe Ser Asp Tyr Ser Ile Ile Asn
        50                  55                  60

Lys Ala Leu Asn Ser Gly His Ile Asp Leu Asn His Phe Gln Asn Tyr
65                  70                  75                  80

Ala Tyr Phe Val Asn Ala Thr Asn Lys Asn Asp Tyr Tyr Leu Ser Ile
                85                  90                  95

Ile Asp Lys Thr Phe Ile Ala Ser Met Asn Met Tyr Ser Lys Asn Leu
            100                 105                 110

Thr Asn Leu Ser Gln Leu Gln Leu Asn Ser Lys Ile Ala Ile Pro Lys
            115                 120                 125

Asp Glu Val Asn Leu Ser Arg Ala Leu Lys Ile Leu Glu Ser Ile Gly
        130                 135                 140

Leu Leu Lys Leu Thr Lys Lys Asp Asn Ile Asn Tyr Asn Phe Thr Thr
145                 150                 155                 160

Asn Asp Ile Arg Glu Asn Tyr Leu Lys Leu Glu Phe Val Asp Val Glu
                165                 170                 175

Ala Asp Asp Val Tyr Ser Val Val Ser Phe Val Asp Ala Ala Phe Val
            180                 185                 190

Asn Leu Asn Leu Asn Phe Asp Phe Lys Asp Ser Asn Ile Leu Tyr Tyr
            195                 200                 205

Asp Asp Pro Ser Lys Tyr Asp Ser Asp Met Tyr Ile Asn Leu Ile Ala
        210                 215                 220

Ala Arg Leu Glu Asp Glu Asp Asn Ser Leu Tyr Lys Thr Ile Ala Glu
225                 230                 235                 240

Ala Tyr Lys Lys Arg Ile Lys Glu Val Val Ser Gly Lys Leu Glu
                245                 250                 255

Gly Ile Ile Ile Asn Tyr
            260

<210> SEQ ID NO 5
<211> LENGTH: 272
<212> TYPE: PRT
<213> ORGANISM: brachyspira hyodysenteriae

<400> SEQUENCE: 5

Met Lys Lys Phe Leu Leu Val Ser Ser Ala Ile Leu Ser Leu Met
1               5                   10                  15

Ile Leu Ser Cys Gly Asn Thr Ser Ser Gly Asp Gln Lys Ile Val Lys
            20                  25                  30

Val Gly Phe Ala Gly Glu Ser Asp Tyr Gln Ile Trp Asp Pro Ile Val
            35                  40                  45
```

-continued

Ala Lys Leu Ala Glu Glu Gly Ile Lys Val Glu Leu Val Ser Phe Ser
 50                  55                  60

Asp Tyr Thr Ile Pro Asn Gln Ala Leu Asn Asp Gly Glu Ile Asp Leu
 65                  70                  75                  80

Asn Ala Phe Gln His Tyr Ala Tyr Phe Asn Asp Glu Val Ser Asn Lys
                 85                  90                  95

Gly Tyr Asp Leu Thr Ala Ile Ala Asp Thr Tyr Ile Ser Ala Met Asn
            100                 105                 110

Ile Tyr Ser Thr Asn Ile Thr Asp Val Lys Glu Leu Lys Asn Gly Asp
        115                 120                 125

Lys Ile Ala Ile Pro Asn Asp Pro Ser Asn Gly Arg Ala Leu Lys
130                 135                 140

Val Leu Gln Ala Ala Gly Ile Ile Lys Val Lys Pro Glu Ala Gly Asp
145                 150                 155                 160

Thr Pro Ser Val Arg Leu Ile Ile Glu Asn Pro Leu Asn Ile Glu Ile
                165                 170                 175

Val Glu Ile Gly Cys Gln Val Leu Phe Thr Gly Val Leu Pro Asp Val
            180                 185                 190

Ala Cys Ala Val Ile Asn Gly Asn Tyr Ala Ile Asp Phe Gly Leu Asn
        195                 200                 205

Pro Gly Ser Asp Tyr Ile Phe Lys Asp Pro Ser Ile Tyr Ser Gly
210                 215                 220

Lys Ser Phe Val Asn Leu Ile Ala Ala Arg Thr Lys Asp Lys Asp Asn
225                 230                 235                 240

Glu Leu Tyr Lys Lys Val Val Glu Thr Tyr Gln Ser Glu Ile Val Glu
                245                 250                 255

Lys Val Tyr Asn Glu Asn Phe Leu Gly Ser Tyr Leu Pro Thr Trp Lys
            260                 265                 270

<210> SEQ ID NO 6
<211> LENGTH: 24
<212> TYPE: DNA
<213> ORGANISM: brachyspira hyodysenteriae

<400> SEQUENCE: 6
tagatgaagc atatgatgat atcg                                        24

<210> SEQ ID NO 7
<211> LENGTH: 24
<212> TYPE: DNA
<213> ORGANISM: brachyspira hyodysenteriae

<400> SEQUENCE: 7
ttctttcttg taaggatcct aata                                        24

<210> SEQ ID NO 8
<211> LENGTH: 24
<212> TYPE: DNA
<213> ORGANISM: brachyspira hyodysenteriae

<400> SEQUENCE: 8
atacggatcc tagtcaactg ctat                                        24

<210> SEQ ID NO 9
<211> LENGTH: 25
<212> TYPE: DNA
<213> ORGANISM: brachyspira hyodysenteriae

<400> SEQUENCE: 9
tcatgcggac atatgtcttc tggtg                                           25

<210> SEQ ID NO 10
<211> LENGTH: 18
<212> TYPE: DNA
<213> ORGANISM: brachyspira hyodysenteriae

<400> SEQUENCE: 10
ggagatactc ctagcgta                                                   18

<210> SEQ ID NO 11
<211> LENGTH: 18
<212> TYPE: DNA
<213> ORGANISM: brachyspira hyodysenteriae

<400> SEQUENCE: 11
ctacaaatga tataagag                                                   18

<210> SEQ ID NO 12
<211> LENGTH: 18
<212> TYPE: DNA
<213> ORGANISM: brachyspira hyodysenteriae

<400> SEQUENCE: 12
gaaagatttg ataaccat                                                   18

<210> SEQ ID NO 13
<211> LENGTH: 18
<212> TYPE: DNA
<213> ORGANISM: brachyspira hyodysenteriae

<400> SEQUENCE: 13 cttaaccta gcataaat                                                    18

<210> SEQ ID NO 14
<211> LENGTH: 24
<212> TYPE: DNA
<213> ORGANISM: brachyspira hyodysenteriae

<400> SEQUENCE: 14
ctatttcatg ccatatggca aatg                                            24

<210> SEQ ID NO 15
<211> LENGTH: 25
<212> TYPE: DNA
<213> ORGANISM: brachyspira hyodysenteriae

<400> SEQUENCE: 15
gccatatatc aggatccaat tctcc                                           25

<210> SEQ ID NO 16
<211> LENGTH: 44
<212> TYPE: DNA
<213> ORGANISM: brachyspira hyodysenteriae

<400> SEQUENCE: 16
ctaatacgac tcactatagg gagaccaagt aggaagataa gaac                      44

<210> SEQ ID NO 17
<211> LENGTH: 44
<212> TYPE: DNA
<213> ORGANISM: brachyspira hyodysenteriae -continued

```
<400> SEQUENCE: 17
ctaatacgac tcactatagg gagagatgat aattccctct aatt        44

<210> SEQ ID NO 18
<211> LENGTH: 44
<212> TYPE: DNA
<213> ORGANISM: brachyspira hyodysenteriae

<400> SEQUENCE: 18
ctaatacgac tcactatagg gagagtcaac tgctatgaga ccgt        44

<210> SEQ ID NO 19
<211> LENGTH: 44
<212> TYPE: DNA
<213> ORGANISM: brachyspira hyodysenteriae

<400> SEQUENCE: 19
ctaatacgac tcactatagg gagaccaaac agctatatac acac        44

<210> SEQ ID NO 20
<211> LENGTH: 24
<212> TYPE: DNA
<213> ORGANISM: brachyspira hyodysenteriae

<400> SEQUENCE: 20
ttatcatttc atatgtcatg taat        24

<210> SEQ ID NO 21
<211> LENGTH: 24
<212> TYPE: DNA
<213> ORGANISM: brachyspira hyodysenteriae

<400> SEQUENCE: 21
cattaaggat cctatggctg atga        24

<210> SEQ ID NO 22
<211> LENGTH: 23
<212> TYPE: PRT
<213> ORGANISM: brachyspira hyodysenteriae

<400> SEQUENCE: 22

Met Asn Lys Lys Ile Phe Thr Leu Phe Leu Val Val Ala Ala Ser Ala
1               5                   10                  15

Ile Phe Ala Val Ser Cys Asn
            20
```

BRACHYSPIRA HYODYSENTERIAE VACCINE

CROSS REFERENCE TO RELATED APPLICATIONS

This application is a continuation of U.S. patent application Ser. No. 10/514,054 abandoned, which is a National Phase entry under 35 U.S.C. § 371 of International Application No. PCT/EP03/04903, filed May 6, 2003 (inactive), which claims priority to European Patent Application No. EP 02076800.8, filed May 8, 2002, all of which are fully incorporated by reference herein.

The text document saved under the file name "Substitute-SequenceListing" created on Mar. 30, 2009 is hereby incorporated by reference.

The present invention relates to nucleic acid sequences encoding a *Brachyspira hyodysenteriae* lipoprotein and to parts of such nucleic acid sequences that encode an immunogenic fragment of such lipoproteins, and to DNA fragments, recombinant DNA molecules, live recombinant carriers and host cells comprising such nucleic acid sequences or such parts thereof. The invention also relates to a *Brachyspira hyodysenteriae* lipoprotein and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic acid sequences or such parts thereof, lipoproteins or immunogenic parts thereof and antibodies against such lipoproteins or immunogenic parts thereof. Also, the invention relates to the use of said lipoproteins in vaccines and for the manufacture of vaccines. Moreover, the invention relates to the use of said nucleic acid sequences, lipoproteins or antibodies for diagnostic or vaccination purposes. Finally the invention relates to diagnostic kits comprising such a nucleic acid, lipoprotein or antibodies against such lipoprotein.

BACKGROUND OF THE INVENTION

*Brachyspira hyodysenteriae* is an anaerobic, oxygen tolerant, Gram-negative spirochete that is strongly β-hemolytic. In the past, *Brachyspira hyodysenteriae* was also known as *Treponema hyodysenteriae* and *Serpulina hyodysenteriae*. It is the etiological agent of swine dysentery, a mucohemorrhagic diarrheal disease of post-weaning pigs. Infection in swine with this bacterium can be suppressed with antimicrobials. However, recent restrictions on the use of antibiotics in animal feed provide impetus for the identification of candidate vaccine antigens as alternatives to the use of antimicrobials.

Swine dysentery (SD) is a mucohemorrhagic diarrheal disease of post-weaning pigs. SD has a major economic impact worldwide. The severity of the symptoms is variable between individuals and herds. The first signs of infection include soft, yellow to gray faeces, loss of appetite and increased rectal temperature in some animals. Subsequent to this, the faeces begin to contain flecks of blood and plugs of mucus. As the disease progresses, the faeces become watery, and prolonged diarrhea may lead to death by dehydration. Faeces containing *B. hyodysenteriae* are ingested by susceptible pigs, after which the organisms survive passage through the acidic conditions of the stomach and reach the large intestine. Experimental evidence suggests that the organism has a chemotactic response to mucus, enabling it to navigate to the colon mucosa where it invades the colon crypts. The large intestine is the major site for water and electrolyte resorption in pigs; damage to the large intestine thus results in colon absorption failure and dehydration.

Diagnosis of SD is based on clinical signs, herd history and isolation of *B. hyodysenteriae* on selective medium. *B. hyodysenteriae* is often difficult to isolate because of its slow growth and anaerobic requirements, a problem exacerbated by poor storage and transportation of samples. Even when isolation is possible, biochemical tests of isolates are unable to differentiate between *B. hyodysenteriae* and *B. innocens*, a non-pathogenic intestinal spirochete. The costly and time consuming nature of enter pathogenic studies in pigs or suitable animal models (such as mice, guinea pigs and chickens) precludes this approach for regular diagnosis.

Several virulence factors of *B. hyodysenteriae* have been identified and their role in the pathogenesis of swine dysentery investigated. For example, the initial colonization of the colon by *B. hyodysenteriae* is facilitated by its chemotactic response to mucus. (Kennedy, M. J., D. K. Rosnick, R. G. Ulrich, and R. J. Yancey. 1988, J. Gen. Microbiol. 134: 1565-1576). (Kennedy, M. J., and R. J. Yancey. 1996, Vet. Microbiol. 49: 21-30).

The importance of chemotaxis was demonstrated by Rosey, (Rosey, E. L., M. J. Kennedy, and R. J. Yancey, Jr. 1996, Infect. Immun. 64: 4154-4162), who showed that a dual flagella mutant was severely attenuated in a murine model. Once the colonization of the swine caecum is established, NADH oxidase is thought to protect the *Brachyspira* from oxygen toxicity. (Stanton, T. B., and N. S. Jensen. 1993, J. Bacteriol. 175: 2980-2987). (Stanton, T. B., and R. Sellwood. 1999, Anaerobe 5: 539-546). This hypothesis is supported by the observation that an NADH oxidase mutant exhibited reduced colonization of the swine caecum. The caecal lesions apparent on pathological examination of chronically infected swine can be induced by administration of *B. hyodysenteriae* haemolysin-containing extracts. Initially, three distinct putative haemolysin genes, tlyA, tlyB and tlyC were cloned and sequenced. (Muir, S., M. B. Koopman, S. J. Libby, L. A. Joens, F. Heffron, and J. G. Kusters. 1992, Infect. Immun. 60: 529-535). (ter Huurne, A. A., S. Muir, M. van Houten, B. A. van der Zeijst, W. Gaastra, and J. G. Kusters. 1994, Microb. Pathog. 16: 269-282). A recent report by Hsu et al. has cast doubt on whether the tly genes actually encode haemolysins and has implicated another gene hlyA in haemolysin production (Hsu, T., D. L. Hutto, F. C. Minion, R. L. Zuerner, and M. J. Wannemuehler. 2001, Infect. Immun. 69: 706-711).

In the search for antigens which elicit a protective immune response, several proteins have been identified which localize to the outer membrane of *B. hyodysenteriae*. A Proteinase K sensitive 16-kDa antigen was localized to the outer membrane, Subsequently the gene encoding this antigen, smpA; was cloned and found not to be expressed in vivo (Thomas, W., R. Sellwood, and R. J. Lysons. 1992, Infect. Immun. 60: 3111-3116). (Sellwood, R., F. Walton, W. Thomas, M. R. Burrows, and J. Chesham. 1995, Vet. Microbiol. 44: 25-35). An extracytoplasmic 39-kDa antigen, Vsp39, was identified by surface iodination as the predominant surface component of *B. hyodysenteriae* (Gabe, J. D., R. E. Chang, R. J. Slomiany, W. H. Andrews, and M. T. Mccaman. 1995, Infect. Immun. 63: 142-148). While the gene encoding Vsp39 has not been cloned, a series of related tandem paralogous genes encoding 39-kDa proteins with 83-90% identity was identified (Gabe, J. D., E. Dragon, R. J. Chang, and M. T. McCaman. 1998, Identification of a linked set of genes in *Serpulina hyodysenteriae* (B204) predicted to encode closely related 39-kilodalton extracytoplasmic proteins. J. Bacteriol. 180: 444-448). (McCaman, M. T., K. Auer, W. Foley, and J. D.

Gabe. 1999, Vet. Microbiol. 68: 273-283). A putative 30-kDa lipoprotein, BmpB, was found to react with convalescent pig sera. No further data of this protein have been published however (Lee, B. J., T. La, A. S. Mikosza, and D. J. Hampson. 2000, Vet. Microbiol. 76: 245-257).

It is therefore clear that there is a need for new and effective vaccines, especially vaccines that provide broad protection.

It is an objective of the present invention to provide novel vaccines for combating

SUMMARY OF THE INVENTION

*Brachyspira hyodysenteriae* infections.

A new locus comprising four genes has now surprisingly been found, which is thought to encode novel surface expressed bacterial lipoproteins. These lipoproteins turn out to be suitable vaccine components in vaccines for combating *Brachyspira hyodysenteriae* infections. The whole locus has now been cloned and sequenced and the sequence is depicted in SEQ ID NO: 1. The locus has been named the blpGFEA-locus, in view of the fact that it encodes four paralogous genes blpG, F, E and A. The organization of the locus is depicted in FIG. 1. The first ORF, blpG encodes a lipoprotein of 265 amino acids with a molecular mass of 30.3 kD. The second ORF, blpF encodes a lipoprotein of 262 amino acids with a molecular mass of 30.8 kD. ORF blpE also encodes a lipoprotein of 262 amino acids, but with a molecular mass of 30.4 kD. Finally, ORF blpA encodes a lipoprotein of 272 amino acids with a molecular mass of 29.9 kD. The intergenic regions are 31, 20 and 78 b.p. respectively.

BRIEF DESCRIPTION OF THE FIGURES

FIG. 3(*b*). Immunoblots probed with rabbit antiserum against BlpA (top left), BlpE (top right), BlpF (bottom left) and BlpG (bottom right). Lanes are as for FIG. 3(*a*). FIG. 3(*c*). Immunoblot of whole cell lysate of *B. hyodysenteriae* (Lane 1) or *B. innocens* (Lane 2) probed with rabbit BlpA antiserum. The positions of molecular mass standards (kD) are indicated on the left.

FIG. 4. Signal peptide regions of the proteins encoded by the blpGFEA locus and of SmpA. Atypical signal peptidase II recognition sites are indicated by boxes with broken lines. The presence of positively charged lysine residues constituting the signal peptide n-regions are indicated by boxes with solid lines. Hydrophobic amino acids that have been found in h-regions that function well are shaded in light grey, whilst those that function less well are shaded in dark grey.

DETAILED DESCRIPTION

Figure 1:
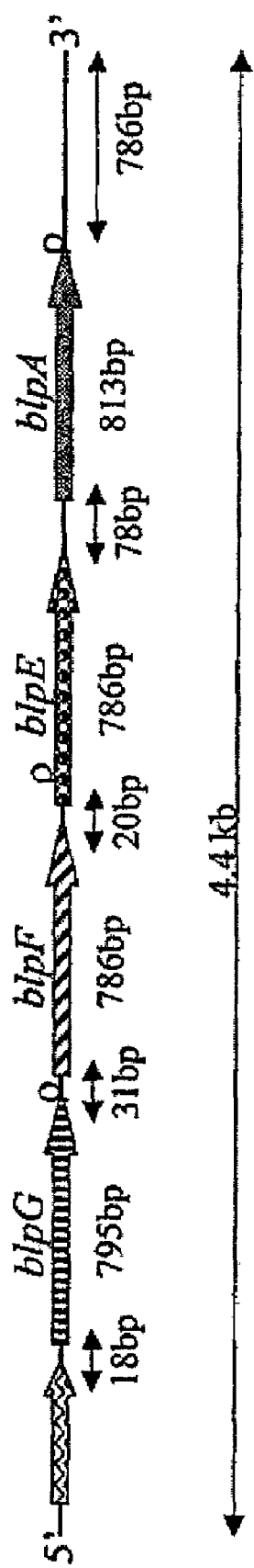
FIG. 1. Organization of the blpGFEA locus. The location and orientation of each gene is indicated with a single headed arrow. The unlabelled arrow at the 5' end of the locus represents a partial open reading frame which shares sequence similarity to lactate dehydrogenase. The locations of putative rho-independent transcriptional terminators are indicated with a rho symbol (ρ). Double headed arrows are used to indicate the sizes of intergenic and non-coding regions.

Genes are to be called paralogous if they diverged after a duplication event. The original quotation is by Walter Fitch (1970, Systematic Zoology 19: 99-113): "Where the homology is the result of gene duplication so that both copies have descended side by side during the history of an organism, (for example, alpha and beta hemoglobin) the genes should be called paralogous (para=in parallel). Where the homology is the result of speciation so that the history of the gene reflects the history of the species (for example alpha hemoglobin in man and mouse) the genes should be called orthologous (ortho=exact)."

This is also well explained in the book "*Fundamentals of Molecular Evolution*" by Li & Graur 1991, Ed. Sinauer Associates, Inc., Sunderland, Mass., USA.

It is well-known in the art, that many different nucleic acid sequences can encode one and the same protein. This phenomenon is commonly known as wobble in the second and especially the third base of each triplet encoding an amino acid. This phenomenon can result in a heterology of about 30% for two nucleic acid sequences still encoding the same protein. Therefore, two nucleic acid sequences having a sequence homology of about 70% can still encode one and the same protein.

Thus, one embodiment relates to a nucleic acid sequence encoding a 30 kD *Brachyspira hyodysenteriae* lipoprotein or a part of said nucleic acid sequence that encodes an immunogenic fragment of said lipoprotein wherein said nucleic acid sequence or said part thereof has at least 70% homology with the nucleic acid sequence of one of the paralogous *Brachyspira hyodysenteriae* lipoprotein genes as depicted in SEQ ID NO: 1.

The 30 kD molecular weight is determined in gel electrophoresis on a polyacrylamide gel. Due to slight variability of molecular weight determination frequently encountered in the art, the molecular weight can vary between 25 and 35 kD. Therefore the molecular weight of the lipoproteins according to the invention should be interpreted as to be 30 kD +/−5 kD.

Preferably, a nucleic acid sequence according to the invention encoding this 30 kD *Brachyspira hyodysenteriae* lipoprotein or a part of that nucleic acid sequence that encodes an immunogenic fragment of that lipoprotein has at least 80%, preferably 90%, more preferably 95% homology with the nucleic acid sequence of one of the paralogous *Brachyspira hyodysenteriae* lipoprotein genes as depicted in SEQ ID NO: 1.

Even more preferred is a homology level of 98%, 99% or even 100%. Nucleotide sequences that are complementary to the sequence depicted in SEQ ID NO 1 or nucleotide sequences that comprise tandem arrays of the sequences according to the invention are also within the scope of the invention.

The level of nucleotide homology can be determined with the computer program "BLAST 2 SEQUENCES" by selecting sub-program: "BLASTN". A reference for this program is Tatiana A. Tatusova, Thomas L. Madden FEMS Microbiol. Letters 174: 247-250 (1999). Parameters used are the default parameters: Reward for a match: +1. Penalty for a mismatch: −2. Open gap: 5. Extension gap: 2. Gap x_dropoff: 50.

Also, one form of this embodiment of the invention relates to nucleic acid sequences encoding a 30 kD *Brachyspira hyodysenteriae* lipoprotein or an immunogenic fragment of that protein comprising an amino acid sequence that has a homology of at least 70%, preferably 80%, 90%, 95%, 98% or even 100% with the amino acid sequence depicted in SEQ ID NO: 2, 3, 4 or 5.

Since the present invention discloses nucleic acid sequences encoding a novel 30 kD *Brachyspira hyodysenteriae* lipoprotein, it is now for the first time possible to obtain this protein in sufficient quantities. This can e.g. be done by using expression systems to express the whole or parts of a paralogous gene encoding the protein or an immunogenic fragment thereof.

Therefore, in a more preferred form of this embodiment, the invention relates to DNA fragments comprising a nucleic acid sequence according to the invention. A DNA fragment is a stretch of nucleotides that functions as a carrier for a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer and for expression of a nucleic acid sequence according to the invention, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment and/or a nucleic acid sequence according to the invention wherein the nucleic acid sequence according to the invention is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6).

Functionally linked promoters are promoters that are capable of controlling the transcription of the nucleic acid sequences to which they are linked. Such a promoter can be the native promoter of the novel gene or another promoter of *Brachyspira*, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of vertebrate origin illustrative useful expression control sequences include the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984), SV40 immediate early promoter (Sprague J. et al., J. Virology 45, 773, 1983), the SV40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well known bovine growth hormone poly-adenylation sequence, the SV40 poly-adenylation sequence, the human cytomegalovirus (hCMV) terminator and poly-adenylation sequences.

Bacterial, yeast, fungal, insect and vertebrate cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are attractive expression systems. Such systems are e.g. described in the French Patent Application with U.S. Pat. No. 2,714,074, and in US NTIS Publication No U.S. Ser. No. 08/043,109 (Hoffman, S, and Rogers, W.: Public. Date 1 Dec. 1993).

A still even more preferred form of this embodiment of the invention relates to Live Recombinant Carriers (LRCs) comprising a nucleic acid sequence encoding a 30 kD *Brachyspira hyodysenteriae* lipoprotein or an immunogenic fragment thereof according to the invention, a DNA fragment according to the invention or a recombinant DNA molecule according to the invention. These LRCs are micro-organisms or viruses in which additional genetic information, in this case a nucleic acid sequence encoding the 30 kD *Brachyspira hyodysenteriae* lipoprotein or an immunogenic fragment thereof according to the invention has been cloned. Pigs infected with such LRCs will produce an immunological response not only against the immunogens of the carrier, but also against the immunogenic parts of the protein(s) for which the genetic code is additionally cloned into the LRC, e.g. the novel 30 kD *Brachyspira hyodysenteriae* lipoprotein gene according to the invention.

As an example of bacterial LRCs, attenuated *Salmonella* strains known in the art can very attractively be used.

Also, live recombinant carrier parasites have i.a. been described by Vermeulen, A. N. (Int. Journ. Parasitol. 28: 1121-1130 (1998)).

Furthermore, LRC viruses may be used as a way of transporting the nucleic acid sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A, 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic add sequence into the genome of a bacterium, parasite or virus of choice, capable of inducing expression of the inserted nucleic acid sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier comprising a nucleic acid molecule encoding a 30 kD *Brachyspira hyodysenteriae* lipoprotein or an immunogenic fragment thereof according to the invention.

A host cell may be a cell of bacterial origin, e.g. *Escherichia coli*, *Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel 30 kD *Brachyspira hyodysenteriae* lipoprotein and to immunogenic fragments thereof according to the invention.

The concept of immunogenic fragments will be defined below.

One form of this embodiment relates i.a. to 30 kD *Brachyspira hyodysenteriae* lipoproteins and to immunogenic fragments thereof, that have an amino acid sequence that is at least 70% homologous to the amino acid sequence as depicted in SEQ ID NO: 2, 3, 4 or 5.

In a preferred form, the embodiment relates to such *Brachyspira lipoproteins* and immunogenic fragments thereof, that have a sequence homology of at least 80%, preferably 90%, more preferably 95% homology to the amino acid sequence as depicted in SEQ ID NO: 2, 3, 4 or 5.

Even more preferred is a homology level of 98%, 99% or even 100%.

Another form of this embodiment relates to such 30 kD *Brachyspira hyodysenteriae* lipoproteins and immunogenic fragments of said protein encoded by a nucleic acid sequence according to the invention.

The level of protein homology can be determined with the computer program "BLAST 2 SEQUENCES" by selecting sub-program: "BLASTP". A reference for this program is Tatiana A. Tatusova, Thomas L. Madden FEMS Microbiol. Letters 174: 247-250 (1999). Matrix used: "blosum62". Parameters used are the default parameters.

Open gap: 11. Extension gap: 1. Gap x_dropoff: 50.

It will be understood that, for the particular proteins embraced herein, natural variations can exist between individual *Brachyspira* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Nal (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity. This explains why *Brachyspira* lipoproteins according to the invention, when isolated from different field isolates, may have homology levels of about 70%, while still representing the same protein with the same immunological characteristics.

Those variations in the amino acid sequence of a certain protein according to the invention that still provide a protein capable of inducing an immune response against infection with *Brachyspira hyodysenteriae* or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in a vertebrate host, e.g. comprises a B- or T-cell epitope. Shortly, an immunogenic fragment is a fragment that is capable of inducing an antigenic response against the 30 kD *Brachyspira hyodysenteriae* lipoprotein according to the invention. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Aced. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application NTIS U.S. Ser. No. 07/005,885). A condensed overview is found in; Shan Lu on common principles: Tibtech 9: 238-242 (1991), Good et al on Malaria epitopes; Science 235: 1059-1062 (1987), Lu for a review; Vaccine 10: 3-7 (1992), Berzofsky for HIV-epitopes; The FASEB Journal 5: 2412-2418 (1991). An immunogenic fragment usually has a minimal length of 8 amino acids, preferably more then 8, such as 9, 10, 12, 15 or even 20 amino acids. The nucleic acid sequences encoding such a fragment therefore have a length of at least 24, but preferably 27, 30, 36, 45 or even 60 nucleic acids.

Therefore, one form of still another embodiment of the invention relates to vaccines for combating *Brachyspira hyodysenteriae* infection, that comprise a 30 kD *Brachyspira hyodysenteriae* protein or immunogenic fragments thereof, according to the invention as described above together with a pharmaceutically acceptable carrier.

Still another embodiment of the present invention relates to the 30 kD *Brachyspira hyodysenteriae* protein according to the invention or immunogenic fragments thereof for use in a vaccine.

Still another embodiment of the present invention relates to the use of a nucleic acid sequence, a DNA fragment, a recombinant DNA molecule, a live recombinant carrier, a host cell or a lipoprotein or an immunogenic fragment thereof according to the invention for the manufacturing of a vaccine for combating *Brachyspira hyodysenteriae* infection.

One way of making a vaccine according to the invention is by growing the bacteria, followed by biochemical purification of the 30 kD *Brachyspira hyodysenteriae* lipoprotein or immunogenic fragments thereof, from the bacterium. This is however a very time-consuming way of making the vaccine.

It is therefore much more convenient to use the expression products of one of the paralogous genes encoding a 30 kD *Brachyspira hyodysenteriae* lipoprotein or immunogenic fragments thereof in vaccines. This is possible for the first time now because the nucleic acid sequence of the paralogous genes encoding a 30 kD lipoprotein is provided in the present invention.

Vaccines based upon the expression products of these genes can easily be made by admixing the protein according to the invention or immunogenic fragments thereof according to the invention with a pharmaceutically acceptable carrier as described below.

Alternatively, a vaccine according to the invention can comprise live recombinant carriers as described above, capable of expressing the protein according to the invention or immunogenic fragments thereof. Such vaccines, e.g. based upon a *Salmonella* carrier or a viral carrier e.g. a Herpesvirus vector have the advantage over subunit vaccines that they better mimic the natural way of infection of *Brachyspira hyodysenteriae*. Moreover, their self-propagation is an advantage since only low amounts of the recombinant carrier are necessary for immunization.

Vaccines can also be based upon host cells as described above, that comprise the protein or immunogenic fragments thereof according to the invention.

All vaccines described above contribute to active vaccination, i.e. they trigger the host's defense system.

Alternatively, antibodies can be raised in e.g. rabbits or can be obtained from antibody-producing cell lines as described below. Such antibodies can then be administered to the pig. This method of vaccination, passive vaccination, is the vaccination of choice when an animal is already infected, and there is no time to allow the natural immune response to be triggered. It is also the preferred method for vaccinating animals that are prone to sudden high infection pressure. The administered antibodies against the protein according to the invention or immunogenic fragments thereof can in these cases bind directly to *Brachyspira hyodysenteriae*. This has the advantage that it decreases or stops *Brachyspira hyodysenteriae* multiplication.

Therefore, one other form of this embodiment of the invention relates to a vaccine for combating *Brachyspira hyodysenteriae* infection that comprises antibodies against the *Brachyspira hyodysenteriae* protein according to the invention or an immunogenic fragment of that protein, and a pharmaceutically acceptable carrier.

Still another embodiment of this invention relates to antibodies against the *Brachyspira hyodysenteriae* protein according to the invention or an immunogenic fragment of that protein.

Methods for large-scale production of antibodies according to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends Biotechn. 12: 262-267., by Clackson, T. & Wells, J. A. (1994) in Trends Biotechn. 12: 173-183, by Marks, J. D. et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S, and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

Still another embodiment relates to a method for the preparation of a vaccine according to the invention that comprises the admixing of antibodies according to the invention and a pharmaceutically acceptable carrier.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)). This way of vaccination is also attractive for the vaccination of pigs against *Brachyspira hyodysenteriae* infection. Therefore, still other forms of this embodiment of the invention relate to vaccines comprising nucleic acid sequences encoding a protein according to the invention or immunogenic fragments thereof, comprising DNA fragments that comprise such nucleic acid sequences or comprising recombinant DNA molecules according to the invention, and a pharmaceutically acceptable carrier.

Examples of DNA plasmids that are suitable for use in a DNA vaccine according to the invention are conventional cloning or expression plasmids for bacterial, eukaryotic and yeast host cells, many of said plasmids being commercially available. Well-known examples of such plasmids are pBR322 and pcDNA3 (Invitrogen). The DNA fragments or recombinant DNA molecules according to the invention should be able to induce protein expression of the nucleotide sequences. The DNA fragments or recombinant DNA molecules may comprise one or more nucleotide sequences according to the invention. In addition, the DNA fragments or recombinant DNA molecules may comprise other nucleotide sequences such as the immune-stimulating oligonucleotides having unmethylated CpG di-nucleotides, or nucleotide sequences that code for other antigenic proteins or adjuvating cytokines.

The nucleotide sequence according to the present invention or the DNA plasmid comprising a nucleotide sequence according to the present invention, preferably operably linked to a transcriptional regulatory sequence, to be used in the vaccine according to the invention can be naked or can be packaged in a delivery system. Suitable delivery systems are lipid vesicles, iscoms, dendromers, niosomes, polysaccharide matrices and the like, (see further below) all well-known in the art. Also very suitable as delivery system are attenuated live bacteria such as *Salmonella* species, and attenuated live viruses such as Herpesvirus vectors, as mentioned above.

Still other forms of this embodiment relate to vaccines comprising recombinant DNA molecules according to the invention.

DNA vaccines can e.g. easily be administered through intradermal application such as by using a needle-less injector. This way of administration delivers the DNA directly into the cells of the animal to be vaccinated. Amounts of DNA in the range between 10 pg and 1000 μg provide good results. Preferably, amounts in the microgram range between 1 and 100 μg are used.

In a further embodiment, the vaccine according to the present invention additionally comprises one or more antigens derived from pig pathogenic organisms and viruses, antibodies against those antigens or genetic information encoding such antigens.

Of course, such antigens can be e.g. other *Brachyspira hyodysenteriae* antigens. It can also be an antigen selected from another other pig pathogenic organism or virus. Such organisms and viruses are preferably selected from the group of Pseudorabies virus, Porcine influenza virus, Porcine parvo virus, Transmissible gastro-enteritis virus, *Rotavirus, Escherichie coli, Erysipelo rhusiopathiae, Bordetelle bronchiseptica, Salmonella cholerasuis, Haemophilus parasuis, Pasteurella multocida, Streptococcus suis, Mycoplasma hyopneumoniae* and *Actinobacillus pleuropneumoniae*.

Vaccines based upon the 30 kD *Brachyspira hyodysenteriae* lipoprotein are also very suitable as marker vaccines. A marker vaccine is a vaccine that allows to discriminate between vaccinated and field-infected pigs e.g. on the basis of a characteristic antibody panel, different from the antibody panel induced by wild type infection. A different antibody panel is induced e.g. when an immunogenic protein present on a wild type bacterium is not present in a vaccine: the host will then not make antibodies against that protein after vaccination. Thus, a vaccine based upon the 30 kD *Brachyspira hyodysenteriae* lipoprotein according to the invention would only induce antibodies against the 30 kD lipoprotein, whereas a vaccine based upon a live wild-type, live attenuated or inactivated whole *Brachyspira hyodysenteriae* would induce antibodies against all or most of the bacterial proteins.

A simple ELISA test, having wells comprising e.g. the purified recombinant nucleoprotein and wells comprising only purified 30 kD *Brachyspira hyodysenteriae* lipoprotein suffices to test serum from pigs and to tell if the pigs are either vaccinated with the 30 kD lipoprotein vaccine or suffered from *Brachyspiral* field infection.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein or an immunogenic fragment thereof, according to the invention and/or antibodies against that protein or an immunogenic fragment thereof, and/or a nucleic acid sequence and/or a DNA fragment, a recombinant DNA molecule, a live recombinant carrier or host cell according to the invention, and a pharmaceutically acceptable carrier.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in pig vaccines are muramyldipeptides, lipopolysaccharides, several glucans and glycans and CARBOPOL ® (a homopolymer).

The vaccine may also comprise a so-called "vehicle". A vehicle is a compound to which the protein adheres, without being covalently bound to it. Such vehicles are i.a. bio-microcapsules, micro-alginates, liposomes and macrosols, all known in the art.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilizers, e.g. to protect degradation-prone proteins from being degraded, to enhance the shelf-life of the vaccine, or to improve freeze-drying efficiency. Useful stabilizers are i.a. SPGA (Bovamik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates. In addition, the vaccine may be suspended in a physiologically acceptable diluent.

It goes without saying, that other ways of adjuvating, adding vehicle compounds or diluents, emulsifying or stabilising a protein are also embodied in the present invention.

Vaccines according to the invention that are based upon the protein according to the invention or immunogenic fragments thereof can very suitably be administered in amounts ranging between 1 and 100 micrograms of protein per animal, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Vaccines according to the invention can be administered e.g. intradermally, subcutaneously, intramuscularly, intrapeditoneally, intravenously, or at mucosal surfaces such as orally or intranasally.

For efficient protection against disease, a quick and correct diagnosis of *Brachyspiral* infection is important.

Therefore it is another objective of this invention to provide diagnostic tools suitable for the detection of *Brachyspiral* infection.

The nucleic acid sequences, the proteins and the antibodies according to the invention are also suitable for use in diagnostics.

Therefore, another embodiment of the invention relates to nucleic acid sequences, proteins and antibodies according to the invention for use in diagnostics.

The nucleic acid sequences or fragments thereof according to the invention can be used to detect the presence of *Brachyspira* in pigs. A sample taken from pigs infected with *Brachyspira* will comprise nucleic acid material derived from said bacterium, including nucleic acid sequences encoding for the protein according to the invention. These nucleic acid sequences will hybridize with a nucleic acid sequence according to the invention. Suitable methods for the detection of nucleic acid sequences that are reactive with the nucleic acid sequences of the present invention include hybridization techniques including but not limited to PCR techniques and NASBA techniques. Thus the nucleic acid sequences according to the invention, in particular the sequences depicted in SEQ ID NO: 1 can be used to prepare probes and primers for use in PCR and or NASBA techniques.

A diagnostic test kit for the detection of *Brachyspira hyodysenteriae* may e.g. comprise tools to enable the reaction of bacterial nucleic acid isolated from the pigs to be tested with these tools. Such tools are e.g. specific probes or (PCR-) primers, also referred to as primer fragments, based upon the nucleic acid sequences according to the invention. If genetic material of *B. hyodysenteriae* is present in the animal, this will e.g. specifically bind to specific PCR-primers and, e.g. after cDNA synthesis, will subsequently become amplified in PCR-reaction. The PCR-reaction product can then easily be detected in DNA gel electrophoresis.

Standard PCR-textbooks give methods for determining the length of the primers for selective PCR-reactions with *Brachyspira hyodysenteriae* DNA. Primer fragments with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in Dieffenbach & Dreksler; PCR primers, a laboratory manual. ISBN 0-87969-447-5 (1995).

Nucleic acid sequences according to the invention or primers of those nucleic acid sequences having a length of at least 12, preferably 15, more preferably 18, even more preferably 20, 22, 25, 30, 35 or 40 nucleotides in that order of preference, wherein the nucleic acid sequences or parts thereof have at least 70% homology with the nucleic acid sequence as depicted in SEQ ID NO: 1 are therefore also part of the invention. Primers are understood to have a length of at least 12 nucleotides and a homology of at least 70%, more preferably 80%, 85%, 90%, 95%, 98%, 99% or even 100%, in that order of preference, with the nucleic acid sequence as depicted in SEQ ID NO: 1. Such nucleic acid sequences can be used as primer fragments in PCR-reactions in order to enhance the amount of DNA that they encode or in hybridization reactions. This allows the quick amplification or detection on blots of specific nucleotide sequences for use as a diagnostic tool for e.g. the detection of *Brachyspira hyodysenteriae* as indicated above.

Another test on genetic material is based upon growth of bacterial material obtained from e.g. a swab, followed by classical DNA purification followed by classical hybridization with radioactively or colour-labeled primer fragments. Colour-labelled and radioactively labeled fragments are generally called detection means. Both PCR-reactions and hybridization reactions are well-known in the art and are i.a. described in Maniatis/Sambrook (Sambrook, J. et al. Molecular cloning: a laboratory manual. ISBN 0-87969-309-6). Thus, one embodiment of the invention relates to a diagnostic test kit for the detection of *Brachyspira hyodysenteriae* nucleic acid sequences. Such a test comprises a nucleic acid sequence according to the invention or a primer fragment thereof.

A diagnostic test kit based upon the detection of antigenic material of the specific *Brachyspira hyodysenteriae* 30 kD lipoprotein and therefore suitable for the detection of *Brachyspira hyodysenteriae* infection may i.a. comprise a standard ELISA test. In one example of such a test the walls of the wells of an ELISA plate are coated with antibodies directed against the 30 kD lipoprotein. After incubation with the material to be tested, labeled anti-*Brachyspira hyodysenteriae* antibodies are added to the wells. A color reaction then reveals the presence of antigenic material from *Brachyspira hyodysenteriae*.

Therefore, still another embodiment of the present invention relates to diagnostic test kits for the detection of antigenic material of *Brachyspira hyodysenteriae*.

Such test kits comprise antibodies against a 30 kD lipoprotein or a fragment thereof according to the invention.

A diagnostic test kit based upon the detection in serum of antibodies against the 30 kD lipoprotein of *Brachyspira hyodysenteriae* and therefore suitable for the detection of *Brachyspira hyodysenteriae* infection may i.a. comprise a standard ELISA test. In such a test the walls of the wells of an ELISA plate can e.g. be coated with the 30 kD lipoprotein. After incubation with the material to be tested, labeled anti-30 kD antibodies are added to the wells. A lack of color reaction then reveals the presence of antibodies against *Brachyspira hyodysenteriae*. Therefore, still another embodiment of the present invention relates to diagnostic test kits for the detection of antibodies against *Brachyspira hyodysenteriae*. Such test kits comprise the 30 kD *Brachyspira hyodysenteriae* lipoprotein or a fragment thereof according to the invention.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a protein according to the present invention in the sample include the enzyme-linked immunosorbent assay (ELISA), immunofluorescence test (IFT) and Western blot analysis.

The proteins or immunogenic fragments thereof according to the invention e.g. expressed as indicated above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the protein according to the invention or an immunogenic fragment thereof according to the present invention, can be prepared by immunizing inbred mice by techniques also known in the art (Kohler and Milstein, *Nature*, 256, 495-497, 1975).

EXAMPLES

Example 1

Bacterial strains and media. *B. hyodysenteriae* B204$^T$ and *Brachyspira innocens* B256$^T$ were used in this study. Brachyspira were grown anaerobically at 37° C. for 48 h on trypticase soy agar containing 5% defibrinated horse blood supplemented with 0.1% yeast extract. Broth cultures of *B.* hyodysenteriae were prepared as described by Wannemuehner et al. (Wannemuehler, M. J., R. D. Hubbard, and J. M. Greer. 1988. Characterization of the major outer membrane antigens of Treponema hyodysenteriae. Infect. Immun. 56: 3032-3039). E. coli strain BL21 (DE3)pLysS (Novagen) was used for production of recombinant hexahistidine fusion proteins. E. coli DH5α was used for cloning and construction of a gene library. E. coli KSS330r⁻[F⁻ Δ(ara-leu) 7697 galE galK ΔlacX74 rpsL(Str$^r$) degP4::Tn5 Ipp5508] (Strauch, K. L., and J. Beckwith. 1988, Proc. Natl. Acad. Sci. USA 85: 1576-1580). was used to check plasmid inserts for the blue halo phenotype. E. coli strains were cultured in Luria-Bertani (LB) broth or on 1.5% LB agar at 37° C. overnight.

Oligonucleotides. Oligonucleotides used in this study are listed in Table 1.

TABLE 1

Oligonucleotides used in this study

| Oligonucletide | Sequence$^a$ | Target |
|---|---|---|
| BAP1424 | 5'-TCA TGC GGA <u>CAT ATG</u> TCT TCT GGT G-3' [SEQ ID NO: 9] | 5' primer used to amplify gene encoding mature BlpA for cloning. Incorporates an NdeI site. |
| BAP1438 | 5'-TAG ATG AAG <u>CAT ATG</u> ATG ATA TCG-3' [SEQ ID NO: 6] | 3' primer used to amplify gene encoding mature BlpA for cloning. Incorporates an NdeI site. |
| BAP1194 | 5'-TTA TCA TTT <u>CAT ATG</u> TCA TGT AAT-3' [SEQ ID NO: 19] | 5' primer used to amplify gene encoding mature BlpE for cloning. Incorporates an NdeI site. |
| BAP1195 | 5'-CAT TAA <u>GGA TCC</u> TAT GGC TGA TGA-3' [SEQ ID NO: 20] | 3' primer used to amplify gene encoding mature BlpE for cloning. Incorporates a BamHI site. |
| BAP1213 | 5'-TTC TTT CTT GTA A<u>GG ATC C</u>TA ATA-3' [SEQ ID NO: 21] | 5' primer used to amplify gene encoding mature BlpF for cloning. Incorporates a BamHI site. |
| BAP1214 | 5'-ATA <u>CGG ATC C</u>TA GTC AAC TGC TAT-3' [SEQ ID NO: 7] | 3' primer used to amplify gene encoding mature BlpF for cloning. Incorporates a BamHI site. |
| BAP1341 | 5'-CTA TTT CAT GC<u>C ATA TGG</u> CAA ATG-3' [SEQ ID NO: 8] | 5' primer used to amplify gene encoding mature BlpG for cloning. Incorporates an NdeI site. |
| BAP1342 | 5'-GCC ATA TAT CA<u>G GAT CC</u>A ATT CTC C-3' [SEQ ID NO: 14] | 3' primer used to amplify gene encoding mature BlpG for cloning. Incorporates a BamHI site. |
| BAP1775 | 5'-<u>CTA ATA CGA CTC ACT ATA GGG AGA</u> CCA AGT AGG AAG ATA AGA AC-3') [SEQ ID NO: 16] and 1532 (5'-GGA GAT ACT CCT AGC GTA-3' [SEQ ID NO: 10] | 3' primer used to amplify a portion of blpA to generate a template for riboprobe synthesis. Incorporates the T7 promoter sequence. |
| BAP1532 | 5'-GGA GAT ACT CCT AGC GTA-3' [SEQ ID NO: 10] | 5' primer used to amplify a portion of blpA to generate a template for riboprobe synthesis. |
| BAP1776 | 5'-<u>CTA ATA CGA CTC ACT ATA GGG AGA</u> GAT GAT AAT TCC CTC TAA TT-3' [SEQ ID NO: 17] | 3' primer used to amplify a portion of blpE to generate a template for riboprobe synthesis. Incorporates the T7 promoter sequence. |
| BAP1534 | 5'-CTA CAA ATG ATA TAA GAG-3' [SEQ ID NO: 11] | 5' primer used to amplify a portion of blpE to generate a template for riboprobe synthesis. |
| BAP1777 | 5'-<u>CTA ATA CGA CTC ACT ATA GGG AGA</u> GTC AAC TGC TAT GAG ACC GT-3' [SEQ ID NO: 18] | 3' primer used to amplify a portion of blpF to generate a template for riboprobe synthesis. Incorporates the T7 promoter sequence. |
| BAP1536 | 5'-GAA AGA TTT GAT AAC CAT-3' [SEQ ID NO: 12] | 5' primer used to amplify a portion of blpF to generate a template for riboprobe synthesis. |

TABLE 1-continued

Oligonucleotides used in this study

| Oligonucletide | Sequence[a] | Target |
|---|---|---|
| BAP1778 | 5'-<u>CTA ATA CGA CTC ACT ATA GGG AGA</u> CCA AAC AGC TAT ATA CAC AC-3' [SEQ ID NO: 19] | 3' primer used to amplify a portion of blpG to generate a template for riboprobe synthesis. Incorporates the T7 promoter sequence. |
| BAP1538 | 5'-CTT AAC CCT AGC ATA AAT-3' [SEQ ID NO: 13] | 5' primer used to amplify a portion of blpG to generate a template for riboprobe synthesis. |

[a]Primers incorporating T7 promoter sequences have the promoter sequence underlined. Primers designed to incorporate restriction enzyme recognition sites have the sites double underlined.

DNA manipulations. Chromosomal DNA from *B. hyodysenteriae* was prepared using the cetyltrimethylammonium bromide precipitation method (Ausubel, F. A., R. Brent, R. E. Kingston, D. D. Moore, J. G. Seidman, J. A. Smith, and K. Struhl. 1991, Current protocols in molecular biology. Greene Publishing and Wiley Interscience, New York), while plasmid DNA was isolated as described by Birnborn and Doly (Birnborn, H. C., and J. Doly. 1979, Nucleic Acids Res. 7: 1513-1523).

Standard methods in molecular biology were performed essentially as described by Sambrook et al. (Sambrook, J., E. F. Fritsch, and T. Maniatis. 1989, Molecular cloning: a laboratory manual. Cold Spring Harbour Laboratory Press, Cold Spring Harbour, N.Y.). Nucleotide sequencing was performed using the BigDye DyeDeoxy Terminator cycle sequencing kit (The Perkin-Elmer Corp., Norwalk, Conn.) and an Applied Biosystems Inc. 373A automated sequencer.

Library construction and colony immunoblotting. Chromosomal DNA from *B. hyodysenteriae* was digested with HindIII and ligated to HindIII-digested pBluescript II KS+ (Stratagene). Competent *E. coli* DH5α was transformed with the ligation mixture and a total of 4,000 colonies was obtained. Colonies were lifted onto nitrocellulose filters and incubated with serum from a pig with culture confirmed *B. hyodysenteriae* infection. Binding of convalescent swine antibodies was detected using alkaline phosphatase-conjugated rabbit-anti pig IgG (Sigma Chemical Co., St. Louis, Mo.). Plasmid inserts from colonies reacting with the convalescent sera were sequenced.

Blue halo assay. Genomic libraries of *B. hyodysenteriae* were constructed using the signal peptide-deficient alkaline phosphatase vector pMG and analyzed as described previously (Blanco, D. R., M. Giladi, C. I. Champion, D. A. Haake, G. K. Chikami, J. N. Miller, and M. A. Lovett. 1991, Mol. Microbiol. 5: 2405-2415).

DNA sequencing and analysis of the blpGFEA locus. Genomic DNA sequence flanking the blue halo vector insert was identified by sequencing SSP-PCR products derived using the method described by Shyamala & Ames 34. (Shyamala, V., and G. Ames. 1989, Gene 84: 1-8). Subsequently, the entire blpGFEA locus was amplified for double stranded DNA sequencing by high fidelity PCR using the Expand high-fidelity PCR kit (Roche). Sequence data were analyzed with Sequencher 3.1 (GeneCodes Corporation, Ann Arbor, Mi.), while DNA and protein database comparisons were made by using the BLAST program of Altschul et al., (Altschul, S. F., G. Warren, W. Miller, E. Myers, and D. J. Lipman. 1990, Basic local alignment search tool. J. Mol. Biol. 215: 403-410). Multiple sequence alignments were performed using PILEUP (Genetics Computer Group [Madison, Wis.] Wisconsin Package).

SDS-PAGE and Western blotting. Proteins were separated with a Bio-Rad Mini-Protean II gel electrophoresis apparatus (Bio-Rad Laboratories, Hercules, Calif.) utilizing a 12.5% polyacrylamide resolving gel and 4% polyacrylamide stacking gel employing the buffer system of Laemmli (Laemmli, U. K. 1970, Nature (London) 227: 680-685). Proteins were transferred onto Immobilon-P membranes (Millipore Corp., Bedford, Mass.) with a Trans-Blot electrophoretic transfer cell (Bio-Rad). The membranes were incubated with a 1/2000 dilution of rabbit antisera. Binding of rabbit antibodies was detected using horse-radish peroxidase conjugated goat-anti rabbit IgG (Silenus Laboratories, Melbourne, Australia).

Recombinant protein expression. PCR was used to amplify the genes encoding the predicted mature length proteins, using primers designed to engineer unique restriction endonuclease sites into the final product (Table 1.). Aliquots of the PCR products were digested with BamHI and/or NdeI. The digested PCR products were ligated into digested and alkaline phosphatase treated pET15-b (Novagen) vectors. Plasmid DNA was isolated from the clones encoding the desired fusion proteins and transformed into the expression strain *E. coli* BL21 (DE3)pLysS. Cultures of the expression strain were grown to an absorbance of 0.6 at 600 nm and induced for 4 h with 5 mM isopropylthio-β-D-galactoside (IPTG; Sigma). Cells were lysed using a French pressure cell (Aminco, Silver Spring, Md.) and recombinant proteins were purified using TALON resin (Clontech, Palo Alto, Calif.) by immobilised metal affinity chromatography according to the manufacturer's instructions. Column eluates were dialyzed overnight against PBS pH 7.2 and concentrated using Centricon-10 (Millipore) concentrators. For antibody cross-reactivity studies the hexahistidine tags were cleaved using 0.4 U of thrombin (Novagen) per 100 μg of recombinant protein and removed by re-incubation with TALON resin (Clontech).

Production of polyclonal antisera. Freund's incomplete adjuvant was emulsified in equal volumes with 100 μg of each of the recombinant proteins and two New Zealand White rabbits were injected subcutaneously with 50 μg of each purified recombinant protein. After 5 weeks, serum was collected from anesthetized rabbits by cardiac puncture.

Northern blotting. RNA was isolated from *B. hyodysenteriae* using TRIZOL (Invitrogen, La Jolla, Calif.) according to the manufacturer's instructions in the presence of RNasin (Promega, Madison, Wis.). Oligonucleotides containing the T7 promoter sequence were designed to amplify approximately 400 bp templates for synthesis of riboprobes complimentary to portions of blpA, blpE, blpF or blpG (Table 1).

Templates for riboprobe synthesis were purified using a QIAQUICK PCR purification kit (Qiagen Pty. Ltd.). Riboprobes were synthesized using a T7/SP6 DIG in vitro transcription kit (Roche) and quantified. Denatured RNA was fractionated on 1.5% agarose gels containing 2% formaldehyde. RNA was transferred by capillary blotting overnight to positively charged nylon membranes (Roche). After transfer of the RNA samples, the membrane was stained with methylene blue to confirm that the RNA had not degraded during isolation or electrophoresis. The membranes were pre-hybridized at 65° C. overnight in a solution containing 50% form amide, 5×SSC, 2% blocking reagent (Roche), 0.5% SDS, 0.1% Seriously, and 200 μg/ml denatured salmon sperm DNA (Sigma). Hybridizations were performed overnight at 65° C. with fresh pre-hybridization buffer containing the probe. Hybridization was detected by chemiluminescence with the CDP-Star reagent (Roche) according to manufacturer's instructions.

TRITON X-114 ™ extraction. *B. hyodysenteriae* outer membrane material was extracted in 0.1% TRITON X-114™ (TX-114) using the method described by Haake et al (Haake, D. A., G. Chao, R. L. Zuerner, J. K. Barnett, D. Barnett, M. Mazel, J. Matsunaga, P. N. Levett, and C. A. Bolin. 2000, Infect. Immun. 68: 2276-2285).

Two dimensional gel electrophoresis (2-DGE). Acetone precipitated outer membrane material from $4 \times 10_8$ brachyspires was resuspended in 460 μl of membrane-specific sample solution [7M urea, 2M thio-urea, 1% tetradecanoylamidopropyl-dimethyl ammino-propane-sulfonate (ASB-14), 2 mM tributylphosphine and 1% carrier ampholytes] by vortexing (Nouwens, A. S., S. J. Cordwell, M. R. Larsen, M. P. Molloy, M. Gillings, M. D. Willcox, and B. J. Walsh. 2000, Electrophoresis 21: 3797-3809). Insoluble material was removed by centrifugation at 12,000×g for 10 min. The 460 μl samples were used to passively rehydrate pH 4-7 immobilized pH gradient dry strips (Bio-Rad). Isoelectric focusing was performed using a step-wise protocol with a final voltage of 3,500V on a Multiphor II (Amersham Pharmacia Biotech, Uppsala, Sweden) equaling a final total of 75 kVh. The second dimension was performed using 8-18% T gradient gels (Walsh, B. J., and B. R. Herbert. 1998, Casting and running vertical slab-gel electrophoresis for 2D-PAGE, p. 245-253. In A. J. Link (ed.), Methods in molecular biology: 2-D proteome analysis protocols, vol. 112. Humana Press Inc., Totowa, N.J.) using a Protean II Multi-Cell (Bio-Rad). The gels were stained with Sypro Ruby (Molecular Probes, Eugene, Oreg.) and gel images were acquired with a Molecular Imager Fx (Bio-Rad).

Sample preparation for mass spectrometry. Protein spots were excised from gels and washed with 50 mM ammonium bicarbonate/100% acetonitrile (60: 40v/v). The gel pieces were dried and rehydrated in a solution containing sequencing grade modified trypsin (Promega, Madison, Wis.) for 1 h at 4° C. Excess trypsin solution was removed and the rehydrated gel pieces immersed in 50 mM ammonium bicarbonate and incubated overnight at 37° C. Eluted peptides were concentrated and desalted using $\mu$-$C_{18}$ Zip-Tips™ (Millipore Corp., Bedford, Mass.) and washed with 10 μl 5% formic acid. The bound peptides were eluted from the Zip-Tip™ in matrix solution (10 mg/ml α-cyano-4-hydroxycinnamic acid [Sigma] in 70% acetonitrile) directly onto the MALDI target plate.

Matrix-assisted laser desorption/ionization time-of-flight (MALDI-TOF) mass spectrometry. MALDI-TOF mass spectra were acquired using a Micromass TofSpec2E equipped with a 337 nm nitrogen laser. All spectra were obtained in reflectron/delayed extraction mode, averaging 256 laser shots per sample. Two-point internal calibration of spectra was performed based upon internal porcine trypsin autolysis peptides (842.5 and 2211.10 [M+H]$^+$ ions). A list of monoisotopic peaks was generated manually and used to search both online and local protein databases, consisting of the translated blpGFEA genes.

Radio-immunoprecipitation and fluorography. 200 μCi of $^3$-[H]palmitic acid (Amersham Life Science) were added to 25 ml of *B. hyodysenteriae* broth culture at a cell density of $10^6$ cells/ml. When a cell density of $10^9$ cells/ml was obtained the cells were harvested by centrifugation. $1.25 \times 10^{10}$ cells were resuspended in RIPA buffer (1% Nonidet P40, 0.5% deoxycholic acid, 10% SDS, 50 mM Tris.Cl pH 8.0) and lysed by sonication. Insoluble material was then removed by centrifugation at 12,000×g. Native BlpA was immunoprecipitated from this mixture by addition of 0.2 ml of anti-BlpA serum and 0.2 ml of Protein A slurry, incubation at 4° C. for 30 min and centrifugation at 12,000×g. The pellet was then washed three times in RIPA buffer before being resuspended in sample buffer for SDS-PAGE. The sample was separated by SDS-PAGE and the gel was treated with Amplify solution (Amersham). An image was obtained by incubating the dried gel in a film cassette with pre-flashed Hyperfilm-MP (Amersham) at −70° C. for 1 week.

Results

Identification and genetic analysis of the blpGFEA locus. Colony immunoblotting of a *B. hyodysenteriae* genomic library with convalescent pig serum identified an *E. coli* clone carrying a plasmid insert with an open reading frame of 813 bp, designated blpA, that encoded a 29.7-kDa protein. Independently, a blue-halo clone was identified which contained part of a 786 bp open reading frame, designated blpE. Chromosome walking using SSP-PCR showed that these two genes were part of a four-gene locus encoding paralogous proteins and spanning 3,545 bp, which was termed blpGFEA (FIG. 1). Analysis of the sequence flanking blpGFEA revealed no additional paralogous genes. No open reading frames were identified in the 786 bp downstream of blpA. The proteins encoded by the blpGFEA locus shared between 61% and 80% identity (Table 2).

TABLE 2

Percentage amino acid identity between
the proteins encoded by the blpGFEA locus

|      | BlpA | BlpE | BlpF | BlpG |
|------|------|------|------|------|
| BlpA | 100  | 61   | 61   | 80   |
| BlpE |      | 100  | 67   | 67   |
| BlpF |      |      | 100  | 61   |
| BlpG |      |      |      | 100  |

The blpGFEA locus has a G+C content of 24.6%; this low G+C content precluded the prediction of putative promoter sequences. However, several putative rho-independent transcriptional terminators were identified (FIG. 1). Oligonucleotide primers flanking the blpGFEA locus were used to check for the presence of the locus in seven serotypes of *B. hyodysenteriae*. A PCR product of identical size to that amplified from B204$^T$ was observed for all serotypes.

Figure 2:
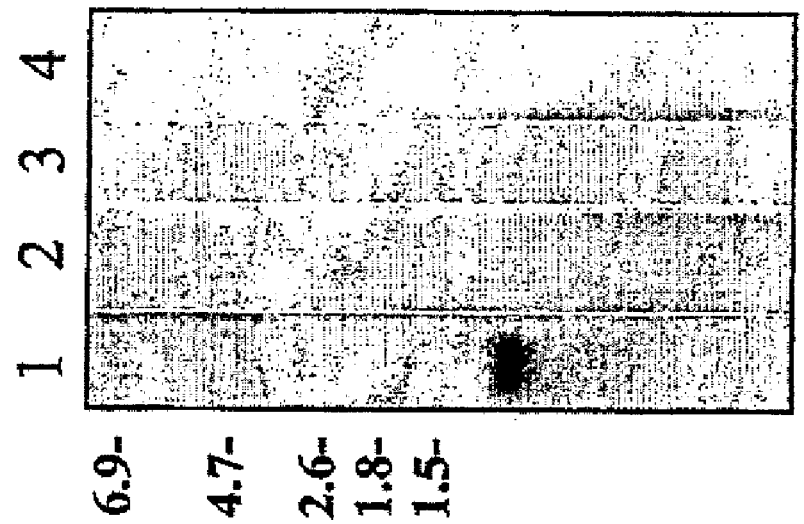
FIG. 2. Northern blot of total RNA from *B. hyodysenteriae* grown under in vitro conditions and hybridized with riboprobes specific for blpA (Lane 1) blpE (Lane 2). blpF (Lane 3) or blpG (Lane 4). The positions of standard RNA size markers (kb) are shown on the left.

Transcriptional analysis of the blpGFEA locus. Riboprobes for each of the genes in the blpGFEA locus were synthesized and used to detect transcription of the individual genes by Northern blotting (FIG. 2). A transcript of 901 bp was detected for blpA, but no transcripts were detected for blpE, blpF or blpG. The size of the detected transcript corresponded to the predicted size of the blpA transcript including the sequence from a putative transcription start point to the beginning of the rho-independent transcriptional terminator.

Figure 3:
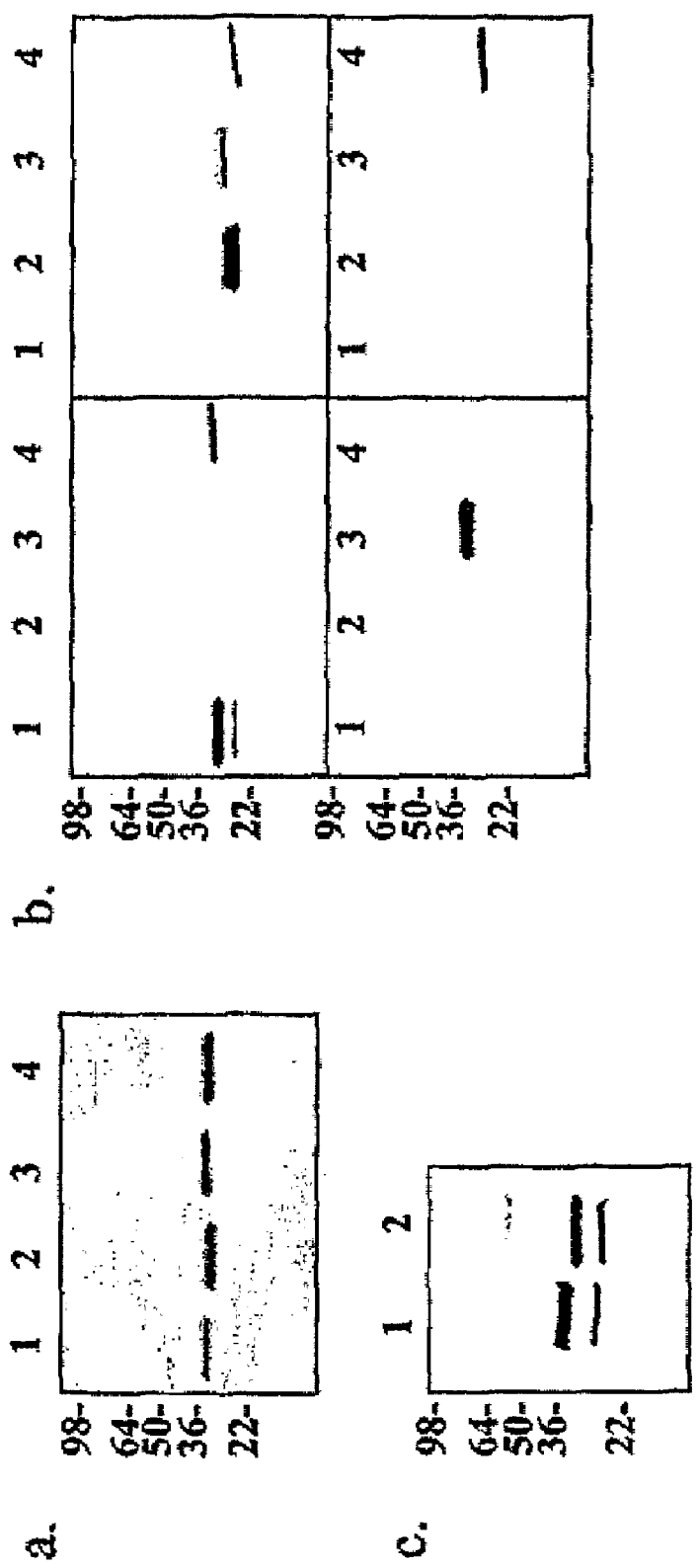
FIG. 3(*a*). Coomasie blue stained recombinant proteins with hexahistidine tags removed: BlpA (Lane 1), BlpE (Lane 2), BIpF (Lane 3) and BlpG (Lane 4).

Immunological analysis of the blpGFEA gene products. Recombinant BlpA, BlpE, BlpF and BlpG fusion proteins were purified and the hexahistidine tags removed (FIG. 3a). The antisera against recombinant BlpF and BlpG were specific and did not cross-react with the other recombinant proteins (FIG. 3b). Antiserum against recombinant BlpA cross-reacted with BlpG and very slightly with BlpE, while antiserum against BlpE cross-reacted with BlpF and BlpG. Only the antisera raised to recombinant BlpA and BlpG recognized proteins from a whole cell lysate of *B. hyodysenteriae*. Western blot analysis with the antiserum against BlpA confirmed that BlpA was also expressed in *B. innocens* (FIG. 3c).

Figure 5:
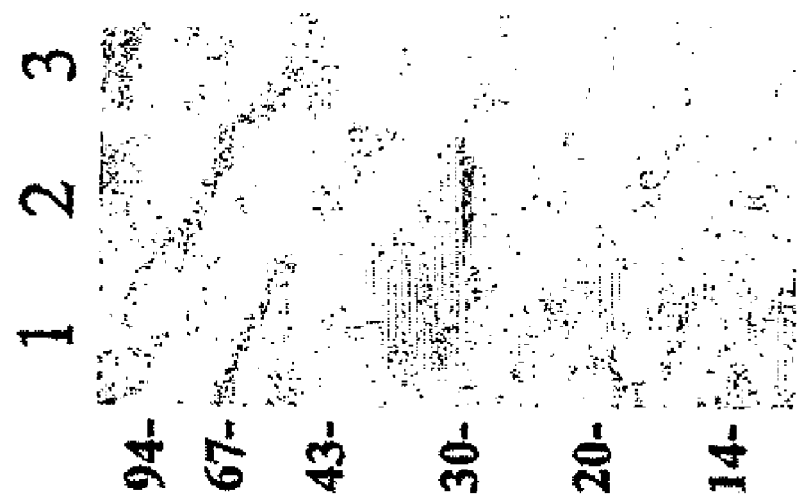
FIG. 5. Autoradiograph of whole cell lysate of *B. hyodysenteriae* grown in the presence of $^3$[H]palmitic acid (Lane 1) and of immunoprecipitated BlpA (Lane 2). Immunoprecipitated BlpA stained with Coomasie brilliant blue (Lane 3). The positions of molecular mass standards (kD) are indicated on the left.

Lipidation of BlpA. Analysis of the amino acid sequence of the proteins encoded by the blpGFEA locus revealed that each protein contained a putative signal peptidase II recognition sequence. It should be noted that the signal peptidase II recognition sequence in spirochetal lipoproteins differs from the consensus established for *E. coli* and other Gram negative bacteria (Haake, D. A. 2000, Microbiology 146: 1491-1504). Notably, the leader sequence in most proteins has similar features; these features include the presence of two positively charged lysine residues constituting the signal peptide n-region and a track of hydrophobic amino acids forming an h-region which extends into the signal peptidase II recognition sequence. The features of the N-terminus of each of the four proteins encoded on the blpGFEA locus are shown in FIG. 4. Radio-immunoprecipitation of BlpA from *B. hyodysenteriae* cultures containing tritiated palmitic acid demonstrated that native BlpA is lipidated by addition of palmitic acid (FIG. 5).

Figure 6:
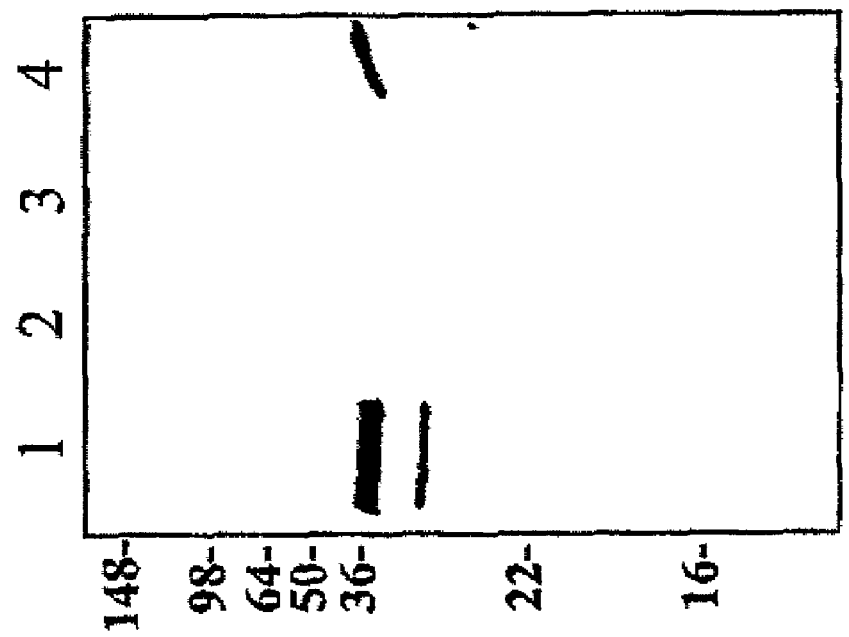
FIG. 6. Western blot of *B. hyodysenteriae* fractions probed with BlpA antiserum. Lane 1,whole cell lysate; Lane 2, protoplasmic cylinder; Lane 3, aqueous phase of TX-114 extraction; Lane 4, detergent phase of TX-114 extraction. The positions of molecular mass standards (kD) are indicated on the left.
Figure 7:
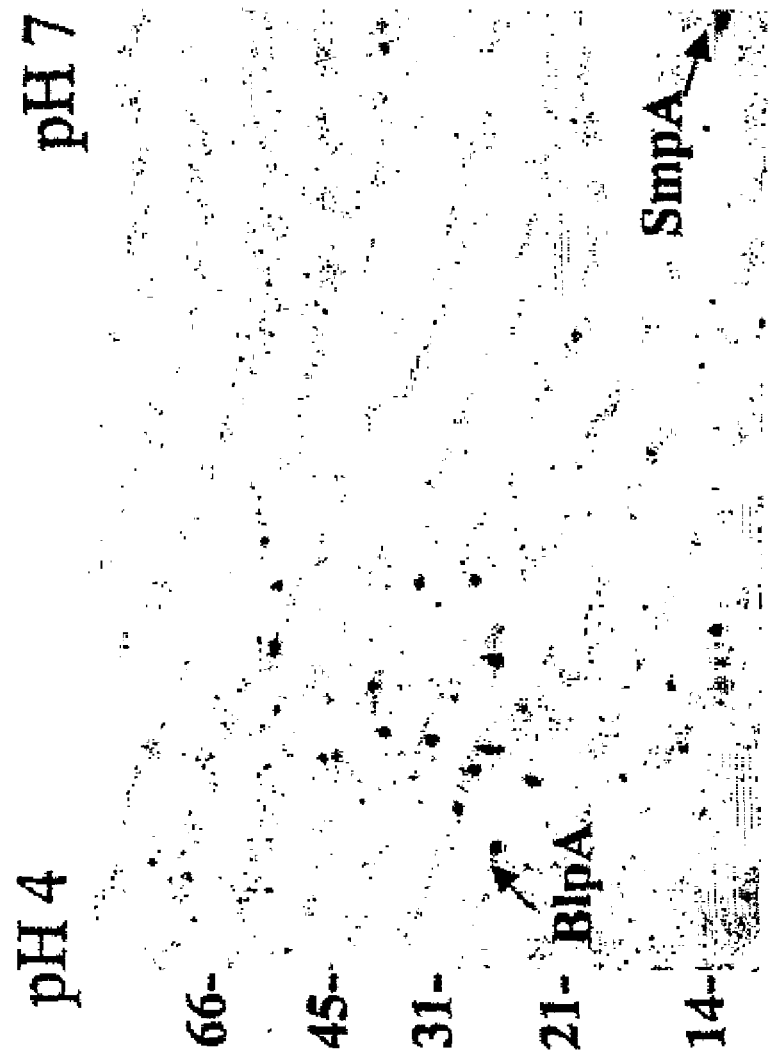
FIG. 7. Two-dimensional gel electrophoresis of the TX-114 detergent phase from *B. hyodysenteriae*. All the protein spots were analysed by MALDI-TOF mass spectrometry and of the proteins encoded by blpGFEA only BlpA was identified (matching peptides covering 30.1% of the sequence). The 16-kDa *Brachyspiral* outer membrane protein SmpA was also identified (matching peptides covering 47.1% of the sequence). The positions of molecular mass standards (kD) are indicated on the left.

Surface localization studies. Isolation of spirochetal outer membranes with TX-114 and the subsequent detection of a protein in the detergent phase is highly indicative of outer membrane location (Haake, D. A. 2000, Microbiology 146: 1491-1504). Western blotting with antisera against recombinant BlpA demonstrated that native BlpA was absent from the protoplasmic cylinder pellet and partitioned exclusively into the TX-114 detergent phase (FIG. 6). The proteins from the *B. hyodysenteriae* TX-114 detergent phase were solubilized in a non-ionic detergent solution designed to increase the solubility of membrane proteins and separated by 2-DGE utilizing a pH 4-7 immobilized pH gradient. We were able to resolve 36 unique spots, of which 34 focused in the 4.0-5.5 pH range (FIG. 7). Each of the resolved proteins was subjected to trypsin digestion and the tryptic peptides analyzed by MALDI-TOF mass spectrometry. Peptide mass matches were obtained to SmpA (FIG. 7), one of only two previously characterized *Brachyspiral* outer membrane proteins (OMPs) for which sequence was available. The inability to detect Vsp39 was most likely due to its rare property of being insoluble in sample buffers containing urea. None of the peptide mass maps matched the tryptic peptide masses predicted for BlpE, BlpF and BlpG. However, a single gel-purified protein corresponding to the predicted translated BlpA sequence was identified (FIG. 7). These data were consistent with the immunological and transcriptional observations, suggesting that only BlpA is expressed under the conditions as currently investigated.

The pattern of transcription observed, where only blpA (the fourth gene in the locus) is transcribed, is consistent with Immunoblotting experiments, which suggested that only BlpA is expressed during infection. The conservation of the locus, both within and between species, strongly suggests that the paralogs are required and expressed under certain conditions, otherwise they would have been lost during divergence. One possible role for the paralogs could be in immune evasion by variation of surface expressed antigens. The genes from the blpGFEA locus that are not expressed could potentially serve as a genetic reservoir for antigenic variation. Also, the other paralogs may be expressed, perhaps transiently, for a particular purpose under specific environmental conditions. For instance, iron limitation is often an inducer of genes involved in the pathogenesis and infection. Other environmental inducers, such as fucose, may (also) be (even more) appropriate for intestinal pathogens. This indicates that a vaccine comprising more than one blp would be preferred over vaccines comprising only one blp.

Example 2

Expression of BlpA in *Salmonella typhimurium* for oral vaccine production. The expression vector pDUMP is described by Cullen, P.A. et al., in Plasmid 49: 18-29 (2003). This expression vector has been designed for the production of lipidated, surface exposed proteins. The section of the open reading frame that encodes the mature portion of BlpA was cloned in pDUMP. The resulting construct was transformed into an attenuated *S. typhimurium* for expression. Western blot analysis demonstrates that BlpA is expressed at high levels in this strain. This *S. typhimurium* strain is designed for use as a live oral vaccine.

Figure 8:
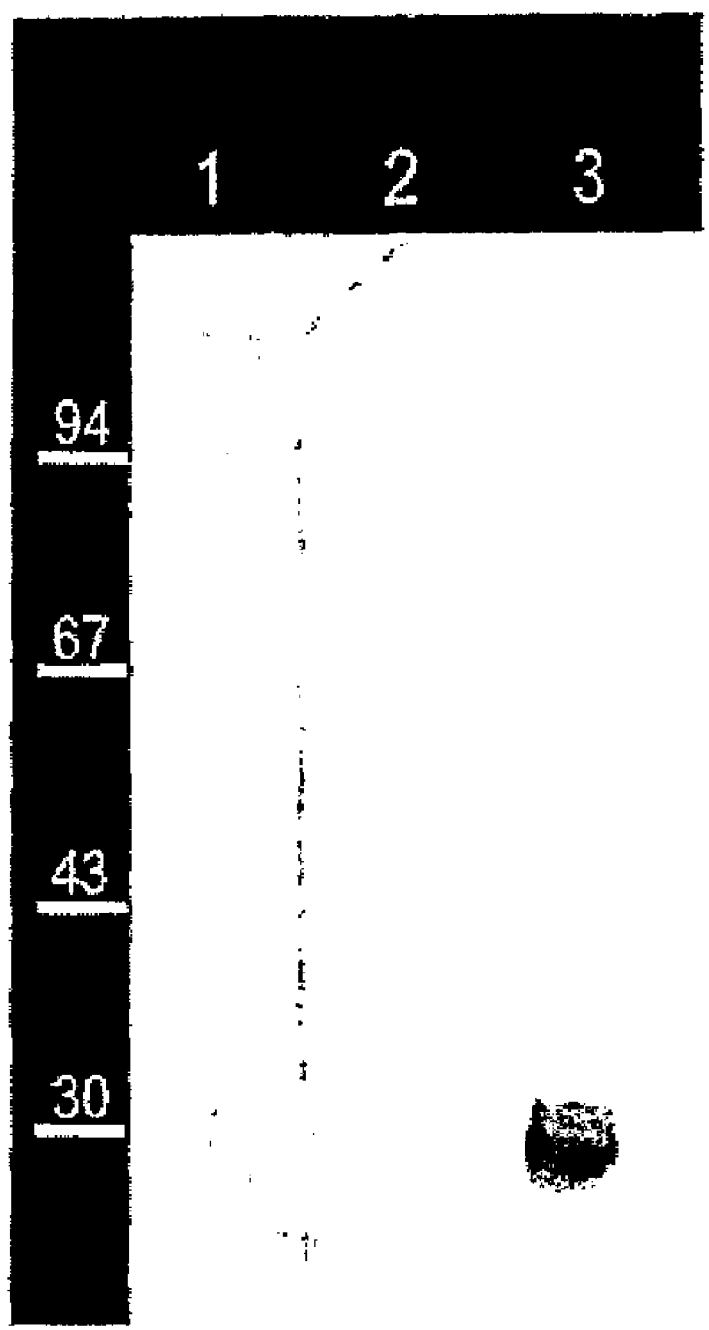
FIG. 8. Expression of BlpA in *Salmonella typhimurium*. Western blot of *S. typhimurium* whole-cell lysate probed with rabbit-anti-BlpA primary antibodies. Lane 1: Low molecular weight markers. Lane 2: *S. typhimurium* containing pDUMP with no insert. Lane 3: *S. typhimurium* containing pDUMP with blpA as the insert.

Result of cloning/expression of blpA in pDUMP:

As can be seen from the Western blot presented in FIG. 8, the *S. typhimurium* strain comprising pDUMP with blpA as an insert produces significant amounts of BlpA, recognized by rabbit-anti-Blpa primary antibodies.

Example 3

Determination of antibody responses to a BlpA delivered by a live attenuated *S. typhimurium* strain. Mice were immunized with lipidated BlpA. This was achieved using a live attenuated aroA mutant stain of *Salmonella typhimurium*. Animals were vaccinated orally in order to stimulate a mucosal immune response. Assays were conducted following vaccination in order to determine the magnitude of both the humoral and mucosal immune response. Indirect ELISA assays are used to detect the presence of lgA (mucosal) and lgM (humoral).

Immunization:
The following groups of 7 mice each were used:
  Naive control mice - immunized with PBS.
  Immunized with *S. typhimurium* with pDUMP (no insert).
  Immunized with *S. typhimurium* pDUMP (blpA).
Mice were starved overnight without food and for 4 hours without water leading up to vaccination. Food and water were made freely accessible immediately after vaccination.
1. Growth broth was inoculated overnight.
2. The culture was diluted and grown to mid-log phase.
3. Cell density was adjusted to ~5×10$^9$cfu/ml.
4. About 150 µl of blood was collected for comparison with post-vaccination samples.
5. 100 µl of 3% sodium bicarbonate was administered orally.
6. Vaccination was done orally with 100 µl of *S. typhimurium*.

Collection of blood and mucosal surface samples (MSS) containing IgA
Collection of blood and MSS is done as follows:
1. Collect blood samples form mice before
2. Remove small intestine from mice.
3. Collect contents by passing 2 ml of 50 mM EDTA, pH7.5 with 0.1 mg/ml of trypsin inhibitor.
4. Adjust volume to 5 ml with 0.15M NaCl
5. Vortex the mixture vigorously and centrifuge for 10 minutes at 3,000 g.
6. Add 50 µl of 100 mM PMSF and spin at 20,000 g for 20 minutes at 4° C.
7. Add 50 µl of 100 mM PMSF and 50 µl of 2% $NaN_3$.
8. Incubate on ice for 15 minutes and add 250 µl of 7% BSA.
9. Freeze at −20° C. until required.

ELISA Assays for the Dectection of IgA
An ELISA assay can be done as follows:
1. Prepare antigen solution at 50 µg/ml.
2. Fill wells with 50 µl of antigen solution and allow it to adsorb to ELISA plates at 4° C. overnight.
3. Block for 30 minutes at room temperature with 0.25% BSA and 0.05% Tween-20 in PBS.
4. Wash three times in distilled water.
5. Add 50 µl of serum or MSS at serial dillutions and incubate for 2 hours at 37° C.
6. Wash three times in distilled water.
7. Add goat-anti-mouse IgA HRP conjugate and incubate for 2 hours at 37° C.
8. Wash three times in distilled water.
9. Develop with ABTS in 0.1 M citrate buffer, pH4.2.
10. Read the reaction in the automated plate reader at $A_{492}$.

The invention claimed is:

1. An expression vector comprising a nucleic acid that encodes the protein sequence set forth in SEQ ID NO: 5.

2. The expression vector of claim 1, wherein said nucleic acid is under the control of a functionally linked promoter.

3. A live recombinant carrier comprising the expression vector of claim 1.

4. A host cell comprising the expression vector of claim 1.

5. A host cell comprising the live recombinant carrier of claim 3.

* * * * *